United States Patent
Liao et al.

(10) Patent No.: US 11,306,363 B2
(45) Date of Patent: Apr. 19, 2022

(54) PROGNOSIS BIOMARKERS FOR TRIPLE-NEGATIVE BREAST CANCER

(71) Applicant: NATIONAL CHIAO TUNG UNIVERSITY, Hsinchu (TW)

(72) Inventors: Kuang-Wen Liao, Hsinchu (TW); Hsien-Da Huang, Taoyuan (TW); Hsiao-Chin Hong, Kaohsiung (TW); Cheng-Hsun Chuang, Tainan (TW)

(73) Assignee: NATIONAL CHIAO TUNG UNIVERSITY, Hsinchu (TW)

( * ) Notice: Subject to any disclaimer, the term of this patent is extended or adjusted under 35 U.S.C. 154(b) by 73 days.

(21) Appl. No.: 16/915,254

(22) Filed: Jun. 29, 2020

(65) Prior Publication Data

US 2021/0404008 A1 Dec. 30, 2021

(51) Int. Cl.
*C12Q 1/6886* (2018.01)

(52) U.S. Cl.
CPC ...... *C12Q 1/6886* (2013.01); *C12Q 2600/118* (2013.01); *C12Q 2600/158* (2013.01); *C12Q 2600/178* (2013.01)

(58) Field of Classification Search
None
See application file for complete search history.

(56) References Cited

PUBLICATIONS

Cobb et al. (Crit Care Med 2002 vol. 30 p. 2711) (Year: 2002).*
Amin et al., "The Eighth Edition AJCC Cancer Staging Manual: Continuing to build a bridge from a population-based to a more "personalized" approach to cancer staging", CA Cancer J Clin, Mar./Apr. 2017, 67: pp. 93-99.
Andrade et al., "Large miRNA survival analysis reveals a prognostic four-biomarker signature for triple negative breast cancer", Genetics and molecular biology, 2020; 43: 1, e20180269, pp. 1-11.
Bertoli et al., "MicroRNAs: New Biomarkers for Diagnosis, Prognosis, Therapy Prediction and Therapeutic Tools forBreast Cancer", Theranostics, 2015, 5(10): pp. 1122-1143.
Dent et al., "Triple-Negative Breast Cancer: Clinical Features and Patterns of Recurrence", Clinical Cancer Research, Aug. 1, 2007, 13(15): pp. 4429.
Fleisher et al., "Current advances in biomarkers for targeted therapy in triple-negative breast cancer," Breast cancer (Dove Medical Press), 2016; 8: pp. 183-197.
Fraley et al., "MCLUST Version 4 for R: Normal Mixture Modeling for Model-Based Clustering, Classification, and Density Estimation", Jun. 2012, Technical Report No. 597, pp. 1-57.
Hamam et al., "Circulating microRNAs in breast cancer: novel diagnostic and prognostic biomarkers", Cell Death Dis., 2017; 8: e3045, pp. 1-12.
Hu et al., "Serum MicroRNA Signatures Identified in a Genome-Wide Serum Microma Expression Profiling Predict Survival Of Non-Small-Cell Lung Cancer", J Clin Oncol., 2010; 28: pp. 1721-1726.
Kandimalla et al. "Genome-wide Discovery and Identification of a Novel miRNA Signature for Recurrence Prediction in Stage II and III Colorectal Cancer", Clinical Cancer Research, Mar. 7, 2018; 24: pp. 3867-3877.
Liang, "Clustering Gene expression Profiles Using Mixture Model Ensemble Averaging Approach", JP Journal of Biostatistics, 2008; 2: pp. 1-25.
Liu et al., "A Comprehensive Immunologic Portrait of Triple-Negative Breast Cancer. Translational oncology", Apr. 2018; 11: 311-329.
Miyoshi et al. "MiR-139-5p as a novel serum biomarker for recurrence and metastasis in colorectal cancer", Mar. 6, 2017, Scientific Report, 7: pp. 1-13.
Ouyang et al. "MicroRNA Profiling Implies New Markers of Chemoresistance of Triple-Negative Breast Cancer", May 2014, PLOS ONE.; 9: pp. 1-8.
Piasecka et al., "MicroRNAs in regulation of triple-negative breast cancer progression", Journal of Cancer Research and Clinical Oncology, 2018; 144: 1401-1411.
Qu et al., Circulating miRNA-21-5p as a diagnostic biomarker for pancreatic cancer: evidence from comprehensive miRNA expression profiling analysis and clinical validation. Scientific reports, May 10, 2017; 7: pp. 1-12.
Sahlberg et al., "A serum microRNA Signature Predicts Tumor Relapse and Survival in Triple-Negative Breast Dancer Patients", Clinical cancer research, Dec. 29, 2014, 21: 1207-1214.
Sestini et al., "Circulating microRNA signature as liquid-biopsy to monitor lung cancer in low-dose computed tomography screening", Oncotarget, Oct. 6, 2015, pp. 32868-32877.
Sestini et al., "Correction: Circulating microRNA signature as liquid-biopsy to monitor lung cancer in low-dose computed tomography screening", Oncotarget, 2019, vol. 10, (No. 57), pp. 6043-6043.
Urabe et al., "Large-scale Circulating microRNA Profiling for the Liquid Biopsy of Prostate Cancer", Clinical Cancer Research, May 15, 2019: pp. 3016-3025.
Voduc et al., "Breast Cancer Subtypes and the Risk of Local and Regional Relapse", Journal of Clinical Oncology, Apr. 1, 2010, 28: pp. 1684-1691.
Volinia et al., "A microRNA expression signature of human solid tumors defines cancer gene targets", Feb. 14, 2006, PNAS, 103: 2257-2261.
Yu et al., "Identification and Validation of Circulating MicroRNA Signatures for Breast Cancer Early Detection Based on Large Scale Tissue-Derived Data", J Breast Cancer, Dec. 2018; 21: pp. 363-370.
Zhang et al., "MicroRNAs as biomarkers for the progression and prognosis of colon carcinoma". International Journal of molecular Medicine, 2018; 42: pp. 2080-2088.
Zhang et al., "Noninvasive Imaging of CD206-Positive M2 Macrophages as an Early Biomarker for Post-Chemotherapy Tumor Relapse and Lymph Node Metastasis", Theranostics, 2017; 7: 4276-4788.

* cited by examiner

*Primary Examiner* — Katherine D Salmon
(74) *Attorney, Agent, or Firm* — Rabin & Berdo, P.C.

(57) ABSTRACT

A microRNA (miRNA) expression signature for predicting triple-negative breast cancer (TNBC) recurrence is provided. The miRNA expression signature consists essentially of hsa-miR-139-5p, hsa-miR-10b-5p, hsa-miR-486-5p, hsa-miR-455-3p, hsa-miR-107, hsa-miR-146b-5p, hsa-miR-324-5p, and hsa-miR-20a-5p.

1 Claim, 36 Drawing Sheets

Specification includes a Sequence Listing.

PROGNOSIS BIOMARKERS FOR TRIPLE-NEGATIVE BREAST CANCER

SEQUENCE LISTING SPECIFIC REFERENCE

This application contains a Sequence Listing submitted via EFS-Web and hereby incorporated by reference in its entirety. The Sequence Listing is named 07_AIPT-107_SE-QCRF.txt, created on Jun. 26, 2020, and 1,599 bytes in size.

BACKGROUND

Technical Field

The disclosure relates to biomarkers of a cancer, especially a breast cancer.

Description of Related Art

Breast cancer (BC) is one of the most common causes of death in women worldwide. BC is not a single disease and is composed of several subtypes, such as luminal A, luminal B, HER2 and triple-negative breast cancer (TNBC). TNBC does not express or expresses low levels of the estrogen receptor (ER), progesterone receptor (PR) and human epidermal growth factor receptor 2 (HER2). TNBC occurs in approximately 10-20% of diagnosed with breast cancers at a younger age of 40-50 years old. TNBC is an advanced multi-drug resistant (MDR) breast cancer with a high recurrence rate within the first three to five years and a short overall survival (OS) rate. The causes behind survival differences are diverse, including genetic predispositions, lifestyle and other environmental factors. Currently, the treatment strategies for TNBC are limited to surgery, chemotherapy, and radiation owing to the lack of effective therapeutic targets. Moreover, due to the high heterogeneity of the tumors, there is a lack of definitive clinical determinants in TNBC-specific diagnostic or prognostic markers.

MicroRNAs (miRNAs) are small noncoding RNAs 18-25 nucleotides that are 18-25 nucleotides in length and negatively regulate gene expression by translational repression or mRNA degradation. Previous evidence has demonstrated that miRNAs facilitate tumor growth, migration, invasion, and angiogenesis as well as the survival of cells and immune evasion via targeting mRNAs. In addition, many studies have reported that miRNAs may function as potential diagnostic and prognostic biomarkers for different cancers. Dominika Piasecka et al. found that upregulated miR-10b, miR-21, miR-29, miR-221/222, and miR-373 and down-regulated miR-145, miR-199a-5p, miR-200 family, miR-203, and miR-205 were significantly associated with mesenchymal transition (EMT) or cancer stem cell (CSC)-like properties and have prognostic value in TNBC patients.

In the field of oncology, biomarkers generally possess three types of clinical relevance: diagnostic values, prognostic values, and predictive values. The prognostic values include the prediction of disease outcomes or risk assessments independent of treatments. The predictive values involve the prediction of responses to treatments as well as sensitive and specific biomarkers of clinical outcomes at a relatively earlier stage. Moreover, the integration of biomarker data using bioinformatics methods would enhance our understanding of biological pathways and regulatory mechanisms associated with diseases. Next-generation sequencing (NGS) and microarrays have increasingly been used to measure the expression levels of miRNAs. Advanced bioinformatics analysis methods with high efficiency, sensitivity and specificity play essential roles in miRNA biomarker development.

The tumor-node-metastasis (TNM) staging system is a classification system based on the characteristics of the tumor, regional lymph nodes, and metastatic sites. In addition, it correlates important tumor characteristics with survival data to help estimate and follow outcomes. However, the current TNM staging system is inadequate for identifying high-risk patients.

SUMMARY

To resolve this problem, an extensive miRNA profiling study on TNBC patients with public datasets was conducted. Each tumor type presents with a unique miRNA signature, which can be used to identify new diagnoses, prognoses and potential biomarkers for personalized medicine. Using systemic and comprehensive bioinformatics methods to train and validate the approach, an 8-miRNA signature that can improve the current TNM staging system and that is superior to the currently offered molecular assays to predict relapse in TNBC patients after surgery was aimed to be identified. Moreover, this signature may have clinical implications in the molecular biomarkers of different cancers, development of targeted therapy, or selection of high-risk cancer patients for adjuvant chemotherapy.

In one aspect, a microRNA (miRNA) expression signature for predicting triple-negative breast cancer (TNBC) recurrence rate of a subject is provided. The miRNA expression signature consisting essentially of hsa-miR-139-5p, hsa-miR-10b-5p, hsa-miR-486-5p, hsa-miR-455-3p, hsa-miR-107, hsa-miR-146b-5p, hsa-miR-324-5p, and hsa-miR-20a-5p.

According to an embodiment, a risk score is calculated by the following formula:

a combination of miRNA panel=(0.02554×expression value of miR-139)+(−0.000005284×expression value of miR-10$b$)+(−0.0003305×expression value of miR-486)+(0.008664×expression value of miR-107)+(0.003201×expression value of miR-324)+(0.001031×expression value of miR-455)+(0.000474×expression value of miR-146$b$)+(−0.001575×expression value of miR-20$a$).

According to another embodiment, the risk score ≥1.602 indicating a high risk of TNBC recurrence rate and death rate.

In another aspect, a method of determining triple-negative breast cancer (TNBC) recurrence rate is provided. The method comprises the following steps. Expression levels of the miRNA expression signature above in a biological sample is measured. The risk score above is then calculated. The TNBC recurrence rate is determined based on the risk score.

The foregoing presents a simplified summary of the disclosure in order to provide a basic understanding to the reader. This summary is not an extensive overview of the disclosure and it does not identify key/critical elements of the present invention or delineate the scope of the present invention. Its sole purpose is to present some concepts disclosed herein in a simplified form as a prelude to the more detailed description that is presented later. Many of the attendant features will be more readily appreciated as the same becomes better understood by reference to the following detailed description considered in connection with the accompanying drawings.

DETAILED DESCRIPTION

Figure 1:
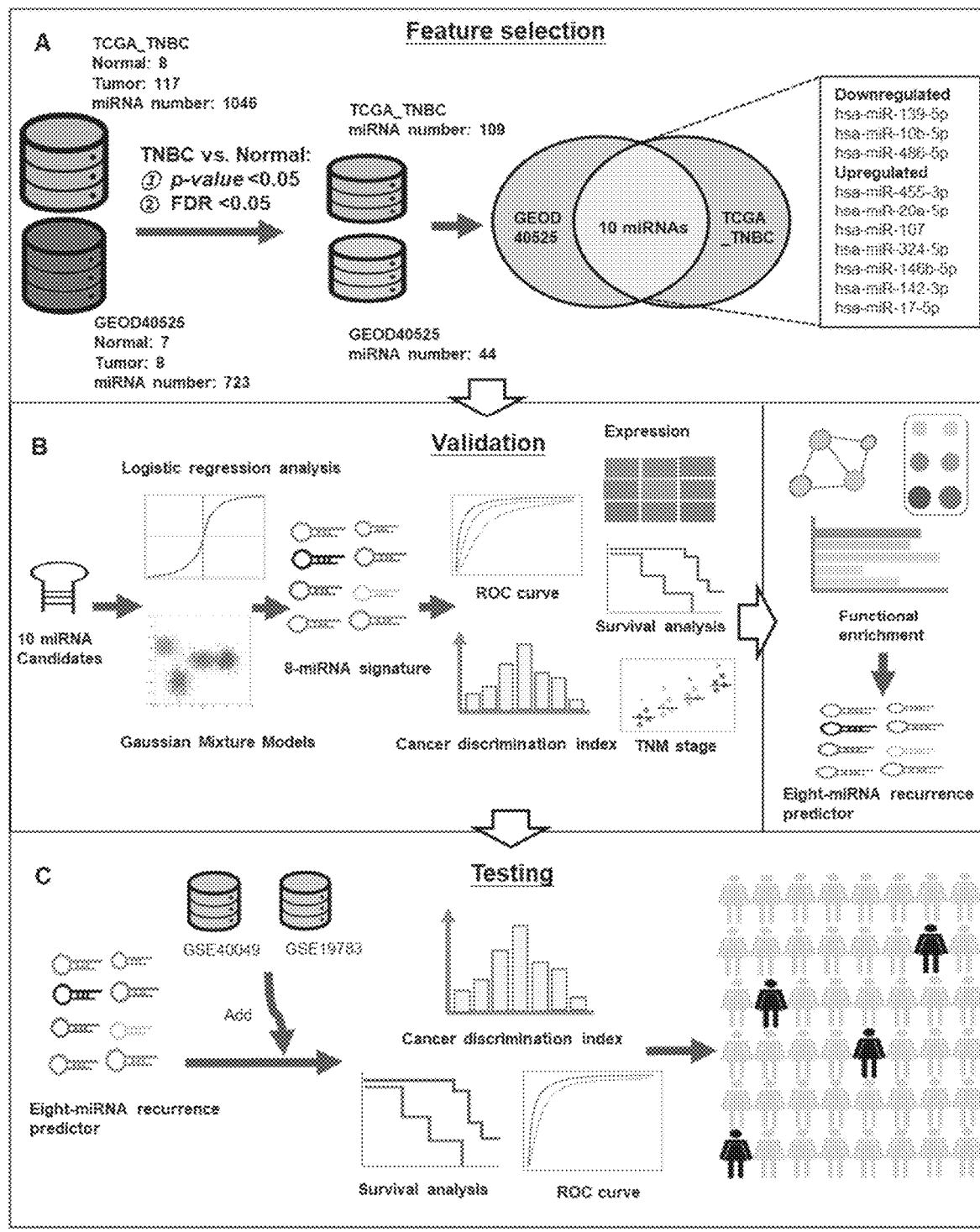
FIG. 1 is a diagram showing a workflow of finding significant miRNAs for predicting TNBC relapse according to an embodiment of this invention.

In the following detailed description, for purposes of explanation, numerous specific details are set forth in order to provide a thorough understanding of the disclosed embodiments. It will be apparent, however, that one or more embodiments may be practiced without these specific details. In addition, the description sets forth the functions of the example and the sequence of steps for constructing and operating the example. However, the same or equivalent functions and sequences may be accomplished by different examples.

Methods
Collection and Processing of Expression Profile Data

Two public datasets were analyzed in the training set: TNBC miRNA sequencing data from TCGA_BRCA level 3 data (The Cancer Genome Atlas (TCGA, https://www.ncbi.nlm.nih.gov/) and GEOD-40525 data from Gene Expression Omnibus (GEO, https://www.ncbi.nlm.nih.gov/gds). All datasets followed the classification system of Voduc et. al, which is based on the immunohistochemical (IHC) semiquantitative analysis of ER, PR, and HER2 expression, as recommended by international guidelines. The TCGA_BRCA data had 117 TNBC (TCGA_TNBC dataset) and 637 non-TNBC (TCGA_non-TNBC dataset) patients. The TCGA_TNBC and GEOD-40525 datasets include 125 patients with corresponding miRNA sequencing data derived from two different platforms. The TCGA_TNBC dataset was conducted through Illumina HiSeq 2000 miRNA sequencing (n=117). The miRNA expression levels, measured by reads per million miRNA mapped (RPM), were first $log_2$ transformed. The GEOD-40525 dataset based on an Agilent-019118 Human miRNA Microarray 2.0 platform (n=8). The top 10 miRNAs (miR-139-5p, miR-10b-5p, miR-486-5p, miR-455-3p, miR-107, miR-146b-5p, miR-17-5p, miR-324-5p, miR-20a-5p and miR-142-3p) were identified after adjustment for multiple comparisons: p-value <0.05 and false discovery rate (FDR)<0.05.

The validation set contained three public datasets, GSE40049, GSE19783 and E-MTAB-1989, from Applied Biosystems SOLiD sequencing (n=24), an Agilent-019118 Human miRNA Microarray 2.0 (n=18) platform and an Affymetrix GeneChip miRNA 2.0 Array (n=18), respectively. The validation data were from GEO (https://www.ncbi.nlm.nih.gov/gds) and ArrayExpress (https://www.ebi.ac.uk/arrayexpress).

Gaussian Mixture and Logistic Regression Models for Predicting Recurrence

Classification was conducted with model-based hierarchical agglomerative clustering based on the Gaussian finite mixture model. The miRNA clusters were classified by the Gaussian mixture model (GMM). Logistic regression analysis was used to construct combined models to predict recurrence. Receiver operating characteristic (ROC) curves were constructed to assess the predictive value of the models by calculating the AUCs.

With the predictive miRNA signature model, the risk score for the 111 TNBC patients was calculated in the TCGA_TNBC dataset. The TNBC patients were classified into recurrence and non-recurrence groups using the median risk score as the cutoff value. The sensitivity and specificity of the miRNA prognostic signature to predict clinical outcome was evaluated by calculating the AUC value of the ROC curve using an R package.

The associations between disease-free survival (DFS) and overall survival (OS) miRNA expression levels were estimated by the Kaplan-Meier method, log-rank test (Mantel-Cox) and Gehan-Breslow-Wilcoxon methods. Differences in survival between the high expression and the low expression miRNAs were analyzed using the two-sided log-rank test.

MiRNA-Target Interactions miRTarBase 7.0 is a comprehensive collection of MTIs that have been validated experimentally. The biological features of miRNA/target duplexes are assessed based on the largest collection of MTIs currently available. miRTarBase uses a pipeline combining text-mining and manual review methods.

Functional Analysis

Gene set enrichment analysis (GSEA) was performed using the software provided by the Broad Institute. Functional enrichment was achieved with MSigDB and the GSEA method. The top 20 biological functions and pathways by using the R packages ggplot2, clusterProfiler [Yu G, Wang L G, Han Y, He Q Y. clusterProfiler: an R package for comparing biological themes among gene clusters. Omics: a journal of integrative biology. 2012; 16: 284-7] and DOSE [Yu G, Wang L G, Yan G R, He Q Y. DOSE: an R/Bioconductor package for disease ontology semantic and enrichment analysis. Bioinformatics (Oxford, England). 2015; 31:

608-9] for the statistical analysis of Gene Ontology (GO) and Hallmark gene sets were found in the gene clusters. The Reactome knowledgebase provides molecular details of signal transduction, transport, DNA replication, metabolism, and other cellular processes as an ordered network of molecular transformations and is an extended version of a classic metabolic map in a single consistent data model.

Statistical Analyses

All statistical analyses were performed using R software (version 3.5.1), the mclust R package [Fraley C, Raftery A, Murphy T, Scrucca L. MCLUST Version 4 for R: Normal Mixture Modeling for Model-Based Clustering, Classification, and Density Estimation; 2012], the pROC package version 1.8 and GraphPad Prism versions 6 and 8 (San Diego, Calif. USA). Venny 2.1 and GENE-E were used to determine the distribution of the differentially expressed miRNAs and their abundance with comprehensive heat mapping software dedicated to displaying gene expression data. For the TCGA, GEO, and ArrayExpress studies, a two-tailed Student's t-test was performed. All statistical tests with a p-value of less than 0.05 were considered significant.

Results

Screening of Candidate miRNAs from Public Datasets

To screen significant biomarkers and verify potential candidate miRNAs in TNBC, NGS and microarray data were incorporated. FIG. 1 is a diagram showing a workflow of finding significant miRNAs for predicting TNBC relapse according to an embodiment of this invention. Part A of FIG. 1 shows 125 TNBC tissues and 15 adjacent normal tissues were obtained from two different datasets (TCGA_TNBC and GEOD-40525). The 10 candidate miRNAs were intersected from these datasets. In part A of FIG. 1, a total of 125 TNBC tissues and 15 adjacent normal tissues were obtained from two different datasets (TCGA_TNBC and GEOD-40525). A total of 1046 and 723 miRNAs were expressed in TCGA_TNBC and GEOD-40525, respectively. Next, the p-value and the FDR threshold as less than 0.05 were set. Then, 109 and 45 miRNAs were reserved in TCGA_TNBC and GEOD-40525, respectively. Finally, 10 candidate miRNAs were intersected in the TCGA_TNBC and GEOD-40525 datasets. The clinicopathological characteristics of the datasets are shown in Table 1 below. A detailed list of the 10 miRNAs generated by the Venn diagram analysis is provided in Table 2 below.

TABLE 1

| Clinicopathologic characteristics of triple-negative breast cancer patients | | |
|---|---|---|
| Data set | TCGA_TNBC | GEOD 40525 data set |
| Number | | |
| TNBC | 117 | 8 |
| Normal | 8 | 7 |
| Total | 125 | 15 |
| Age (year) | 57.42 ± 14.56 | N/A |
| Preservation type | Fresh tissue | Fresh tissue |
| TNM Stage | | |
| I | 21 | N/A |
| II | 68 | N/A |
| III | 21 | N/A |
| IV | 1 | N/A |
| Others | 6 | N/A |
| Lymph node metastasis | | |
| Present | 74 | 5 |
| Absent | 37 | 3 |
| Others | 6 | 0 |
| Distant metastasis | | |
| Present | 4 | N/A |
| Absent | 107 | N/A |
| Others | 6 | N/A |
| Number of deaths | 96 | N/A |
| Median survival (month) | 25.4 | N/A |
| Follow-up period (Day) | | |
| Median | 858 | N/A |
| Range | 1-3472 | N/A |
| Platform | Illumina HiSeq 2000 miRNA Sequencing Illumina Genome Analyzer miRNA Sequencing | Agilent 019118 Human miRNA Micro array 2.0 |

N/A: not available.
Mean ± standard deviation (SD) were presented.

TABLE 2

The expression of ten candidate miRNAs in TNBC tissue between the TCGA_TNBC and GEOD-40525 datasets.

| Data sets | | TCGA_TNBC | | | GEOD_40525 | | |
|---|---|---|---|---|---|---|---|
| microRNA | Chromosome | Log2 Fold Change | p-value | FDR | Log2 Fold Change | p-value | FDR |
| Down-regulated | | | | | | | |
| hsa-miR-139-5p | 11q13.4 | −2.895735451 | 8.33E−33 | 9.08E−31 | −2.662765892 | 3.76E−04 | 1.60E−02 |
| hsa-miR-10b-5p | 2q31.1 | −2.511149588 | 2.59E−32 | 1.41E−30 | −2.779048673 | 4.60E−04 | 1.58E−02 |
| hsa-miR-486-5p | 8p11.21 | −4.248281522 | 3.08E−09 | 8.39E−08 | −1.778231191 | 7.94E−04 | 1.91E−02 |
| Up-regulated | | | | | | | |
| hsa-miR-455-3p | 9q32 | 3.309861939 | 3.19E−02 | 3.91E−02 | 2.688322067 | 9.74E−04 | 2.13E−02 |
| hsa-miR-20a-5p | 13q31.3 | 1.950986771 | 4.29E−02 | 4.62E−02 | 1.738424993 | 3.08E−03 | 4.36E−02 |
| hsa-miR-107 | 10q23.31 | 1.000952191 | 6.88E−03 | 1.79E−02 | 0.883928962 | 3.40E−03 | 4.38E−02 |
| hsa-miR-324-5p | 17p13.1 | 1.785810283 | 7.72E−03 | 1.87E−02 | 0.885061916 | 4.45E−03 | 5.26E−02 |
| hsa-miR-146b-5p | 10q24.32 | 0.94811004 | 3.38E−02 | 3.92E−02 | 1.951810829 | 4.45E−03 | 5.26E−02 |
| hsa-miR-142-3p | 17q22 | 1.986602322 | 4.99E−02 | 4.99E−02 | 2.661047195 | 5.23E−03 | 5.00E−02 |
| hsa-miR-17-5p | 13q31.3 | 2.453964607 | 2.03E−02 | 3.07E−02 | 1.900494005 | 4.49E−04 | 1.71E−02 |

FDR: False-discovery rate

In part B of FIG. 1, these 8 miRNAs analyzed by expression level, Kaplan-Meier curves, TNM classification and GSEA for functional validation. These 10 candidates were used to verify the miRNA signature by logistic regression and generalized method of moments (GMM) analysis. Afterward, an 8-miRNA signature was established according to the area under the ROC curve (AUC) value for tumor relapse. Since the 8-miRNA signature may be a prognostic biomarker, an independent study of GSE40049 and GSE19783 was used to validate its predictive accuracy. Furthermore, data were separately analyzed for these 8 miRNAs by expression level, Kaplan-Meier curves, TNM classification and GSEA for functional validation. In part C of FIG. 1, the GSE40049 and GSE19783 were used to test the predictive accuracy. High-risk groups of TNBC patients, who require active treatment to increase their survival rate, were identified according to the prediction results.

Figure 2A:
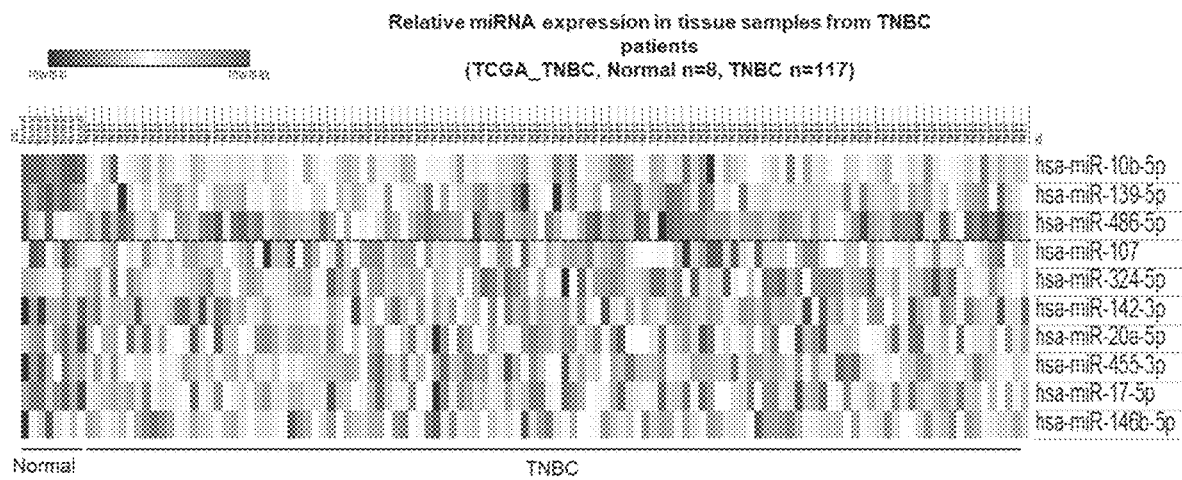
FIGS. 2A-2D show diagrams of the expression patterns of the 10 candidate miRNAs in TNBC tissue samples.
Figure 2B:
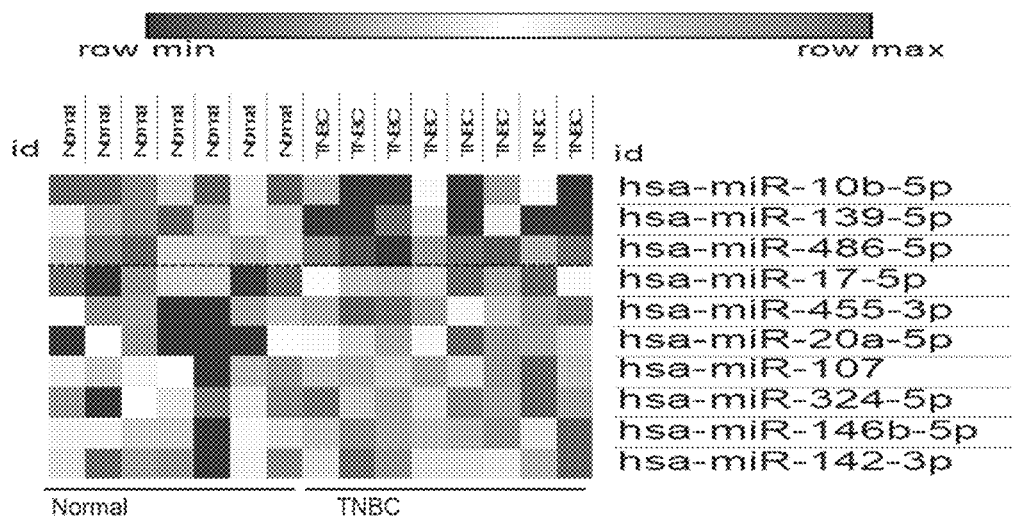
Figure 2C:
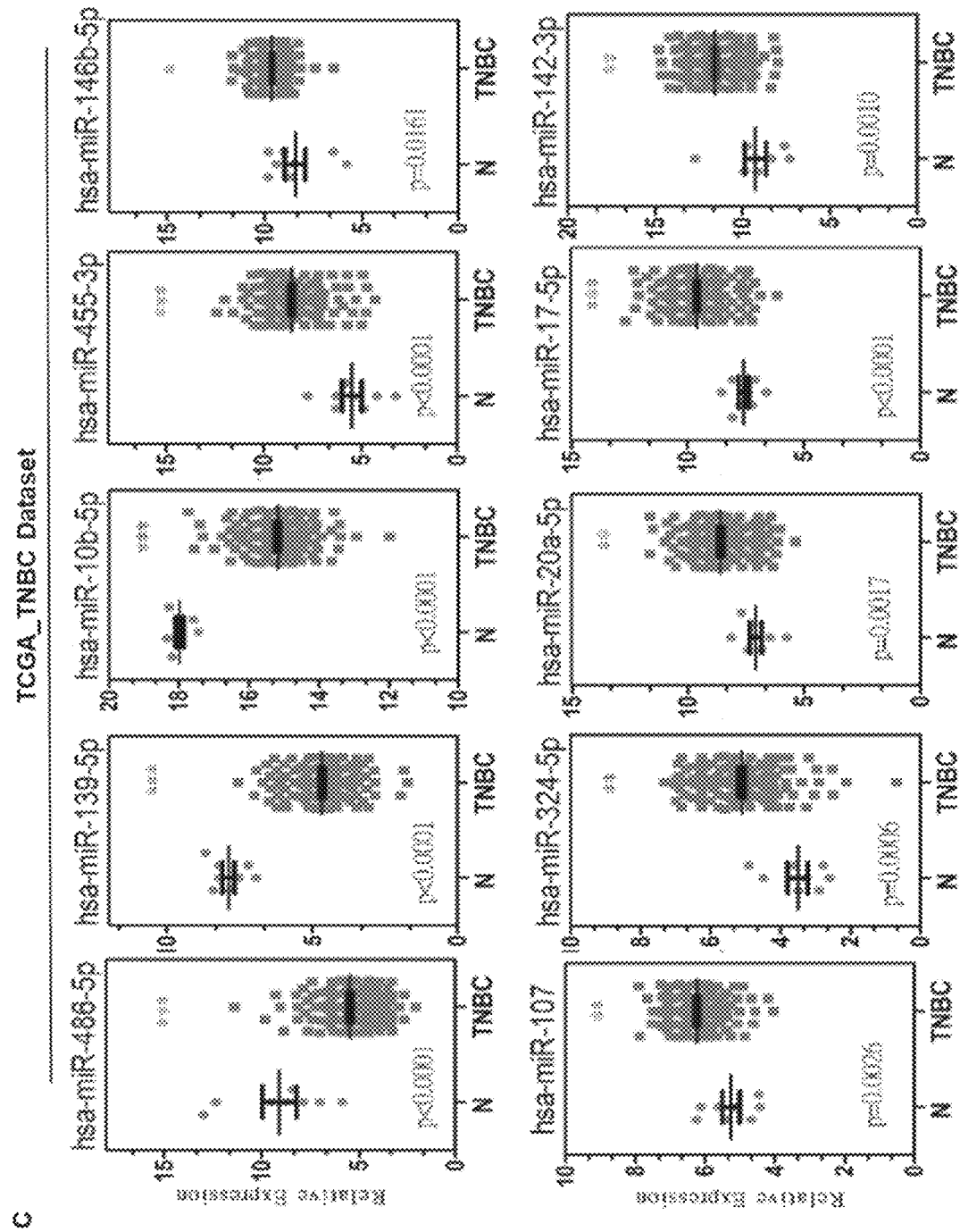
Figure 2D:
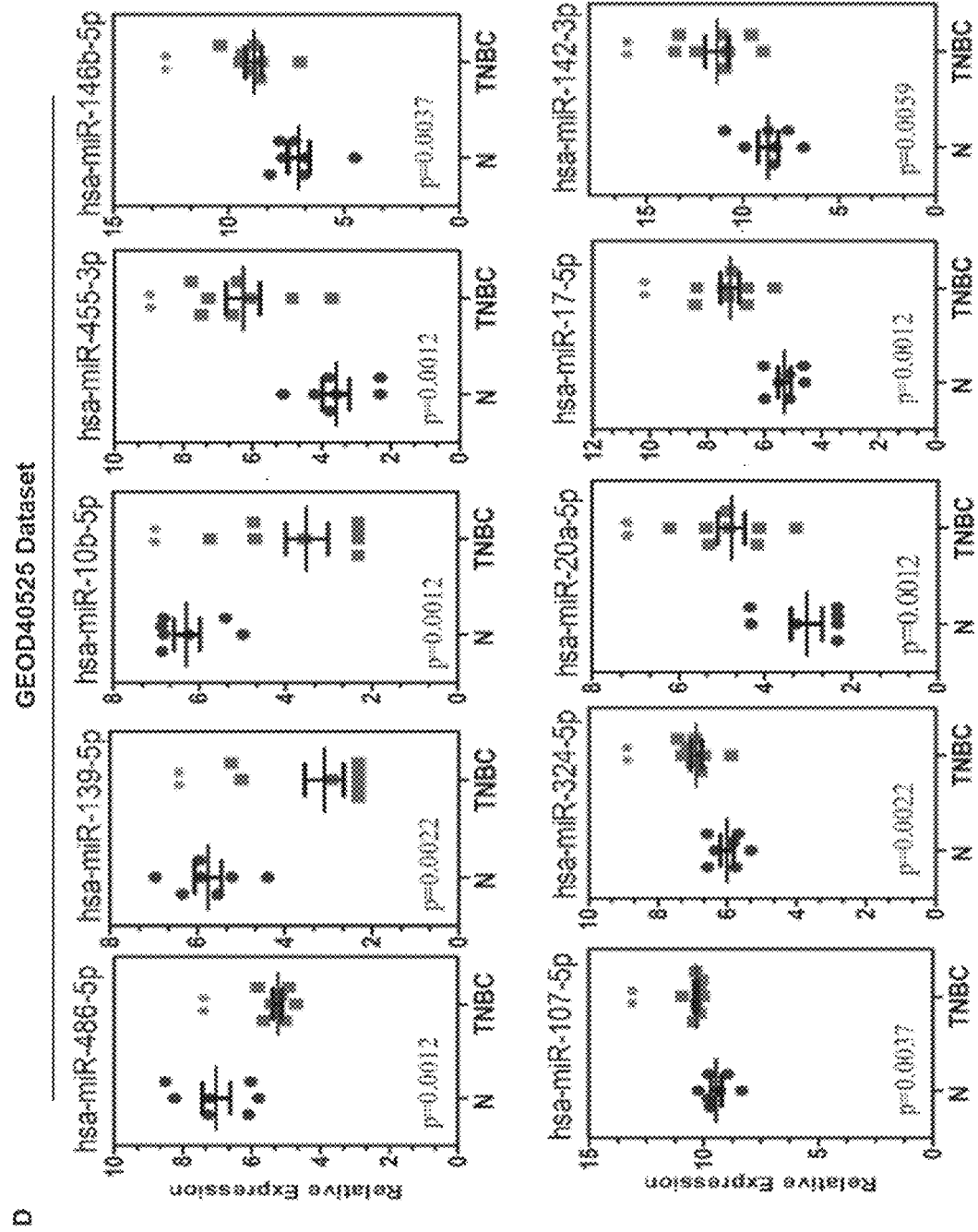

A heatmap was generated representing the expression of the 10 candidate miRNAs distinguished from adjacent normal and tumor tissues for both the TCGA_TNBC and GEOD-40525 datasets combined. FIGS. 2A-2D show diagrams of the expression patterns of the 10 candidate miRNAs in TNBC tissue samples. In FIG. 2A, the expression of meta-signature miRNA between TNBC and non-cancer groups (adjacent normal tissue). In FIG. 2B, heatmap of miRNA array expression by the GEOD-40525 dataset. The expression of 10 meta-signature miRNA between TNBC and non-cancer groups (adjacent normal tissue). In FIG. 2C, the expression of 10 miRNAs between 8 adjacent normal (N) and 117 triple-negative breast cancer (TNBC) tissues from TCGA_TNBC dataset. In FIG. 2D, the expression of 10 miRNAs between 7 adjacent normal (N) and 8 triple-negative breast cancer (TNBC) tissues from GEOD-40525 dataset. The p-value were calculated using the Student's t-test. *p<0.05; p<0.01; *p<0.0001.

In FIGS. 2A-2B, a heatmap was generated representing the expression of the 10 candidate miRNAs distinguished from normal and tumor tissues for both the TCGA_TNBC and GEOD-40525 datasets combined. The expression levels of hsa-miR-486-5p, hsa-miR-139-5p and hsa-miR-10b-5p were upregulated, and the expression levels of hsa-miR-107, hsa-miR-146b-5p, hsa-miR-142-3p, hsa-miR-1'7-5p, hsa-miR-455-3p, hsa-miR-324-5p and hsa-miR-20a-5p were downregulated in both the TCGA_TNBC and GEOD-40525 datasets. In FIGS. 2C-2D, the comparisons of the expression levels of the 10 candidate miRNAs between the tumor and adjacent normal groups revealed that the differences were statistically significant (all p-value <0.05) in the TCGA_TNBC and GEOD-40525 datasets.

Based on the above observations, the specificity and sensitivity of the 10 miRNAs for diagnosis was assessed by ROC analysis. The results are listed in Table 3 below.

TABLE 3

Area under the ROC curve for individual miRNAs from the TCGA_TNBC and GEOD-40525 datasets between adjacent normal and TNBC tissue samples.

| Model set | TCGA_TNBC | p-value | GEOD-40525 | p-value |
|---|---|---|---|---|
| miR-139-5p | 0.9959 | <0.0001 | 0.9464 | 0.003830 |
| miR-10b-5p | 0.9968 | <0.0001 | 0.9643 | 0.002635 |
| miR-486-5p | 0.9217 | <0.0001 | 0.9821 | 0.001790 |
| miR-455-3p | 0.9145 | <0.0001 | 0.9107 | 0.007799 |
| miR-324-5p | 0.8665 | 0.0005449 | 0.9464 | 0.003830 |
| miR-142-3p | 0.8504 | 0.0009443 | 0.9107 | 0.007799 |
| miR-146b-5p | 0.7553 | 0.01595 | 0.9286 | 0.005499 |
| miR-107 | 0.8194 | 0.002574 | 0.9286 | 0.005499 |
| miR-20a-5p | 0.8323 | 0.001682 | 0.875 | 0.01512 |
| miR-17-5p | 0.9135 | <0.0001 | 0.9643 | 0.002635 |

Figure 3:
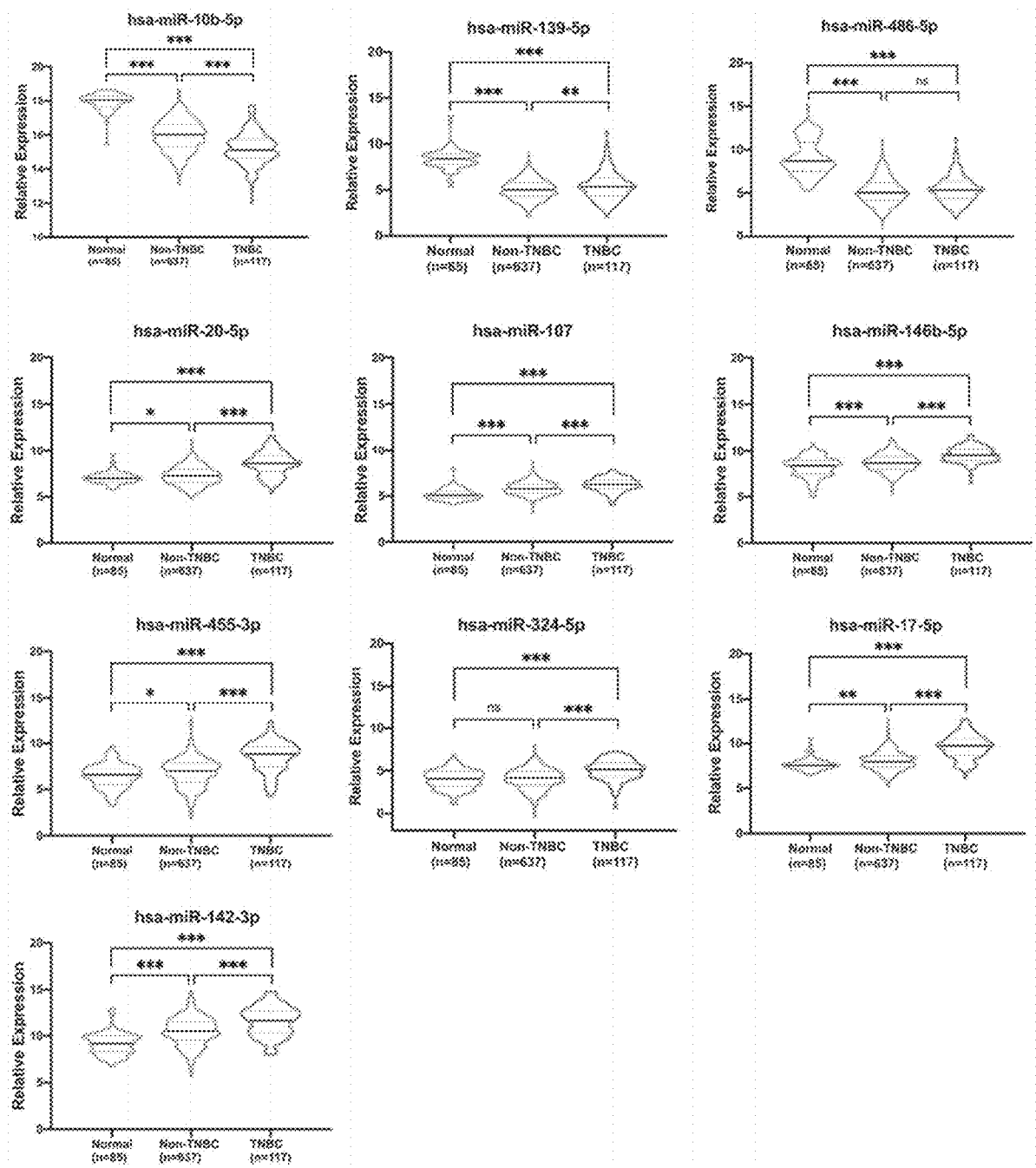
FIG. 3 shows patterns of expression levels of ten miRNAs between normal, TNBC and non-TNBC patients from TCGA_TNBC dataset.

FIG. 3 shows patterns of expression levels of ten miRNAs between normal, TNBC and non-TNBC patients from TCGA_TNBC dataset. *p<0.05; p<0.01; *p<0.0001, and ns is not significant. The bell-shaped curve of ten miRNAs between 85 normal (including 8 and 77 adjacent normal of TNBC and non-TNBC), 117 TNBC and 637 non-TNBC cases from TCGA_TNBC dataset. In the down-regulated miRNAs (hsa-miR-10b-5p, hsa-miR-139-5p, and hsa-miR-486-5p), hsa-miR-486-5p were not significant between TNBC with non-TNBC patients in 10 candidates. The hsa-miR-20-5p, hsa-miR-107, hsa-miR-146b-5p, hsa-miR-455-3p, hsa-miR-324-5p, hsa-miR-17-5p, hsa-miR-142-3p were extremely significant in 7 upregulated miRNAs between TNBC with non-TNBC patients The p-value were calculated using the Student's t-test. The results showed that these 10 candidate miRNAs were quite different in TNBC and non-TNBC patient samples.

These results suggested that the expression levels of aberrantly expressed miRNAs were consistent among individual studies (TCGA_TNBC and GEOD-40525). Thus, these 10 miRNA candidates might be a promising biomarker in patients with TNBC.

Establishment of the 8-miRNA Signature for TNBC Recurrence Prediction with the Training Set To implement predictive modeling, logistic regression analysis was used to evaluate the association between the expression values of each of the 10 miRNA candidates as well as the AUC values that were screened in the survival analysis for patient DFS. There were a total of 1023 formulas from the logistic regression model of the 10 miRNA candidates. Furthermore, decisive GMM-based clustering, which is an extremely popular approach and has a good clustering performance, was used [Ficklin S P, Dunwoodie L J, Poehlman W L, Watson C, Roche K E, Feltus FAJSr. Discovering condition-specific gene co-expression patterns using gaussian mixture models: a cancer case study. 2017; 7: 1-11; Liang FJJJB. Clustering gene expression profiles using mixture model ensemble averaging approach. 2008; 2: 57-80; Liu Z, Song Y-q, Xie C-h, Tang ZJS, Image, Processing V. A new clustering method of gene expression data based on multivariate finite Gaussian mixture models. 2016; 10: 359-68]. Then, gene sets were clustered by the GMM (instead of the 1023 formulas) and AUCs into eight clusters in our proposed algorithm. Afterward, one of the eight clusters that had a higher AUC was selected as the signature to predict the relapse of TNBC patients. Hence, a miRNA candidate risk score model for recurrence was developed by integrating the expression data of the 8 miRNAs.

Figure 4A:
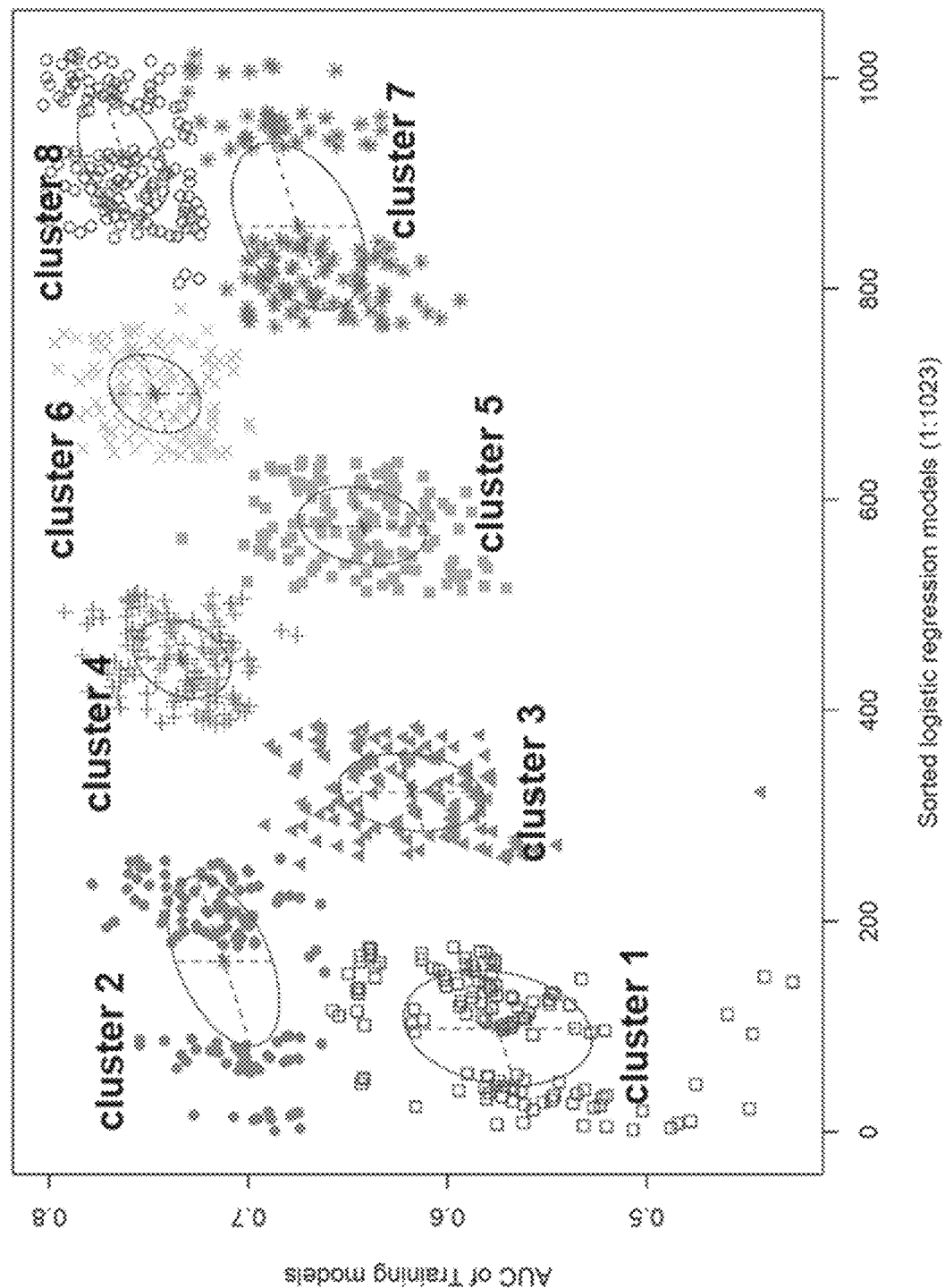
FIGS. 4A-4B show patterns of AUC and 1023 logistic regression models based on Gaussian finite mixture models.
Figure 4B:
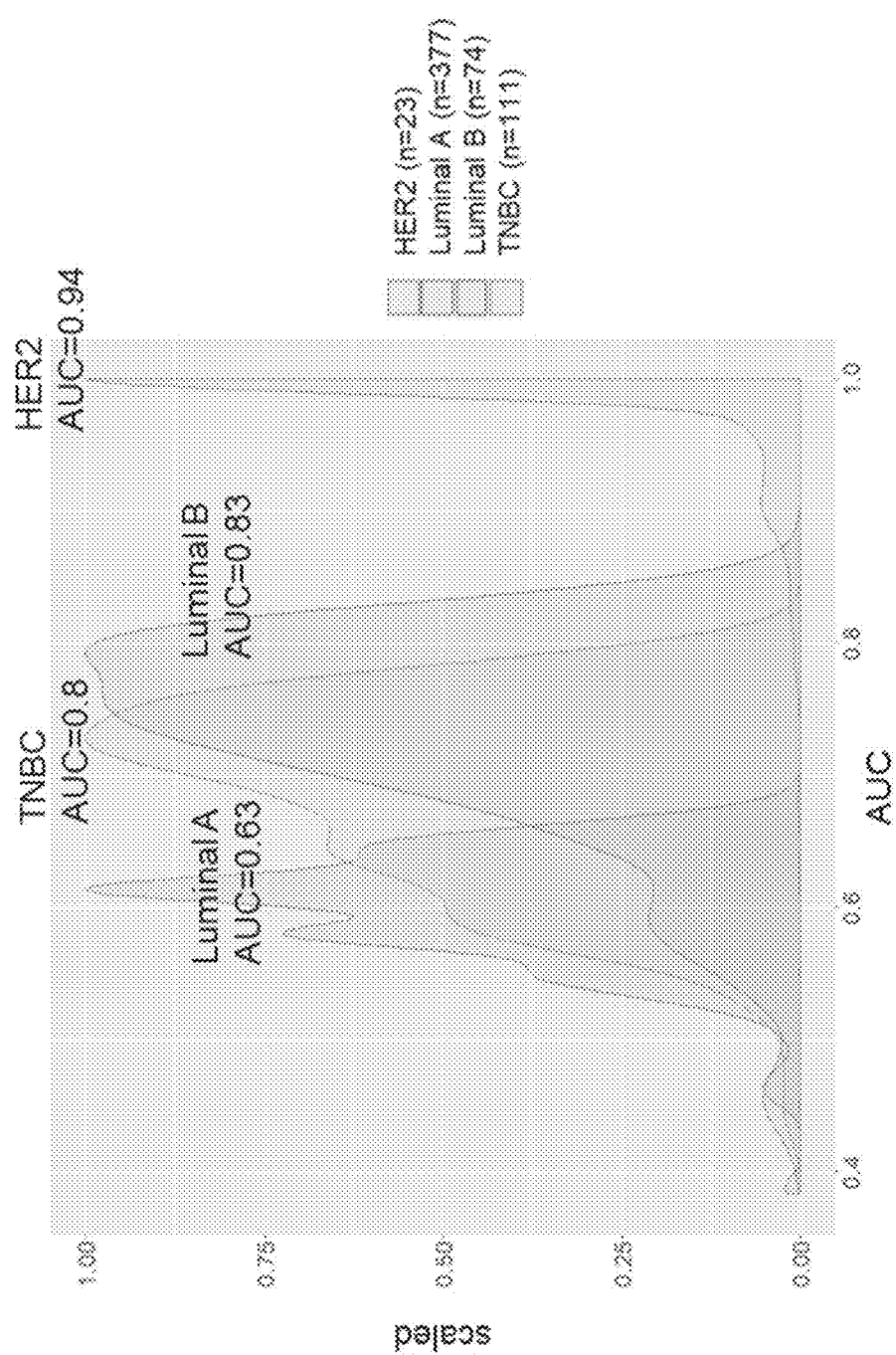

FIGS. 4A-4B show patterns of AUC and 1023 logistic regression models based on Gaussian finite mixture models. In FIG. 4A, patterns of logistic regression model correlated with AUC scores were identified by mixture Gaussian. There are eight clusters of 1023 combinations. The hsa-miR-139-5p, hsa-miR-107, hsa-miR-486-5p, hsa-miR-10b-5p, hsa-miR-146b-5p, hsa-miR-455-3p, hsa-miR-20a-5p and hsa-miR-324-5p signature showed an average accuracy of 0.8031 by the GMM classifier in one of the 1023 formulas. Additionally, the accuracy of miRNAs as well as the 8-miRNA and any 7-miRNA signature to distinguish between recurrent and non-recurrent patients in the TCGA_TNBC dataset by a ROC test is provided in Table 4 below. In FIG. 4B, a total of 1023 combinations correlated with AUC scores in four breast cancer subtypes were shown. This formula was also used to predict and compare the AUC values of the luminal A (AUC=0.63), luminal B (AUC=0.83), HER2 (AUC=0.94) and TNBC (AUC=0.8) subtypes, as shown in FIG. 4B. The results suggested that the AUC value of these 10 candidates in HER2, luminal B, and TNBC patients were better than that in luminal A patients for relapse. However, the AUC values of 8-miRNA combinations in TNBC were limited to 0.8 and were less than those of the other subtypes.

TABLE 4

Area under the ROC curve for seven and eight miRNAs from three public datasets between patients with TNBC recurrence and no recurrence.
TCGA_TNBC in training set

| Model set | Number | miRNA combinations | AUC |
|---|---|---|---|
| Model_1 | 7 | RNR~miR-139 + miR-10b + miR-486 + miR-107 + miR-324 + miR-455 + miR-146b | 0.7560847 |
| Model_2 | 7 | RNR~miR-139 + miR-10b + miR-486 + miR-107 + miR-324 + miR-455 + miR-20a | 0.7846561 |
| Model_3 | 7 | RNR~miR-139 + miR-10b + miR-486 + miR-107 + miR-324 + miR-146b + miR-20a | 0.7481481 |
| Model_4 | 7 | RNR~miR-139 + miR-10b + miR-486 + miR-107 + miR-455 + miR-146b + miR-20a | 0.8005291 |
| Model_5 | 7 | RNR~miR-139 + miR-10b + miR-486 + miR-324 + miR-455 + miR-146b + miR-20a | 0.7724868 |
| Model_6 | 7 | RNR~miR-139 + miR-10b + miR-107 + miR-324 + miR-455 + miR-146b + miR-20a | 0.8015873 |
| Model_7 | 7 | RNR~miR-139 + miR-486 + miR-107 + miR-324 + miR-455 + miR-146b + miR-20a | 0.7994709 |
| Model_8 | 7 | RNR~miR-10b + miR-486 + miR-107 + miR-324 + miR-455 + miR-146b + miR-20a | 0.7402116 |
| Model_9 | 8 | RNR~miR-139 + miR-10b + miR-486 + miR-107 + miR-324 + miR-455 + miR-146b + miR-20a | 0.8031746 |

To validate the prognostic role of this 8-miRNA signature, the miRNA risk score was calculated as follows:

the combination of miRNA panel=(0.02554×expression value of miR-139)+(−0.000005284×expression value of miR-10b)+(−0.0003305×expression value of miR-486)+(0.008664×expression value of miR-107)+(0.003201×expression value of miR-324)+(0.001031×expression value of miR-455)+(0.000474×expression value of miR-146b)+(−0.001575×expression value of miR-20a).

Figure 5A:
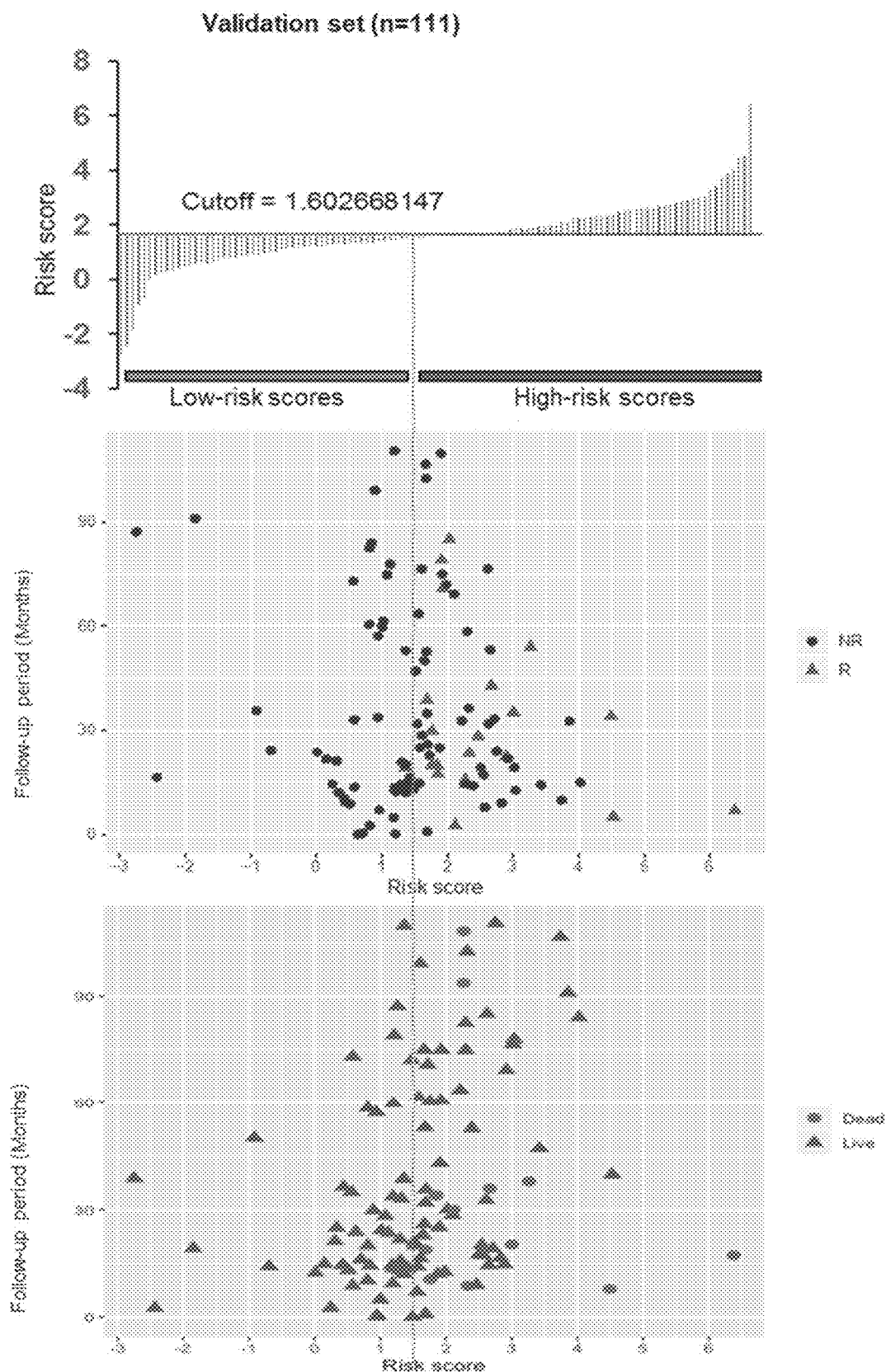
FIGS. 5A-5E show diagrams of the Predictive value of the 8-miRNA signature in 111 TNBC patients.
Figure 5B:
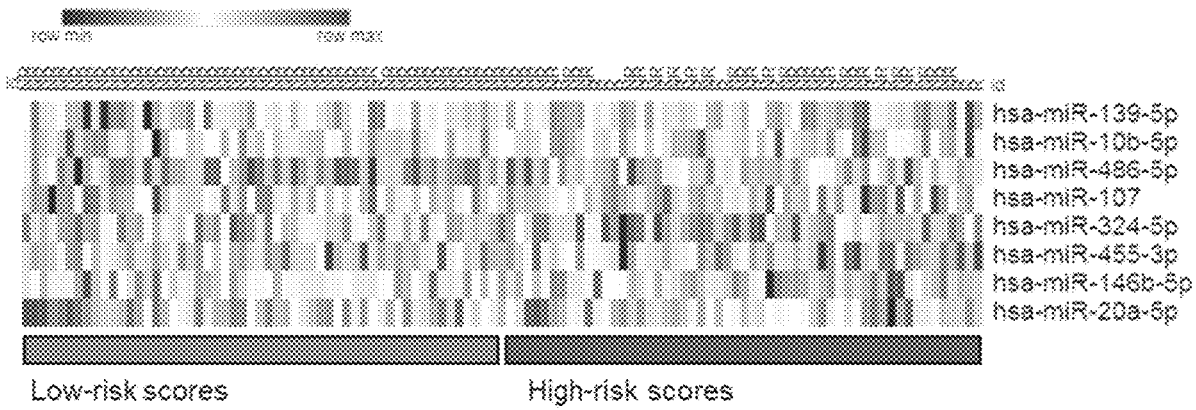
Figure 5C:
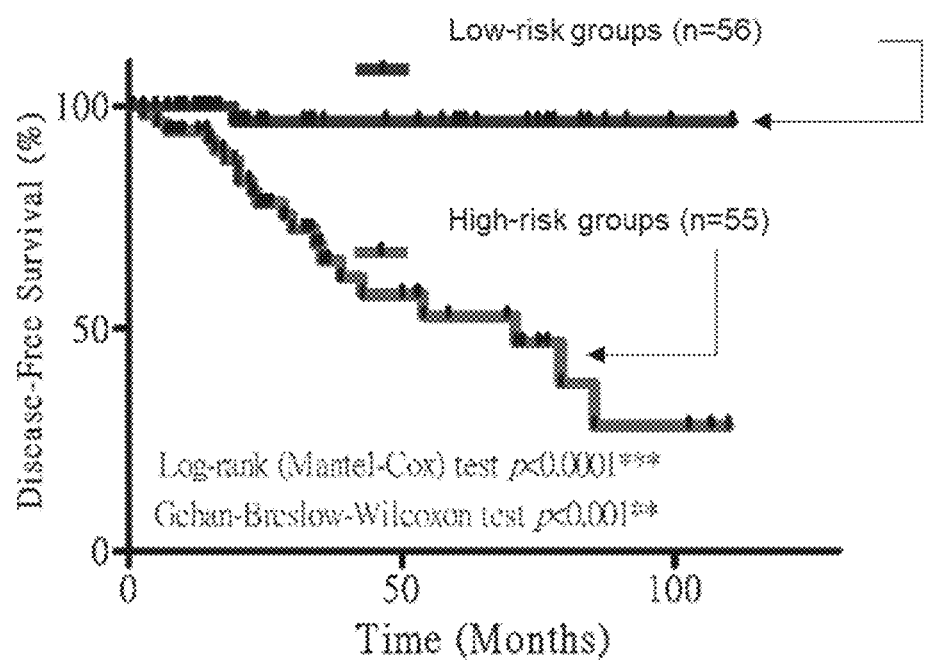
Figure 5D:
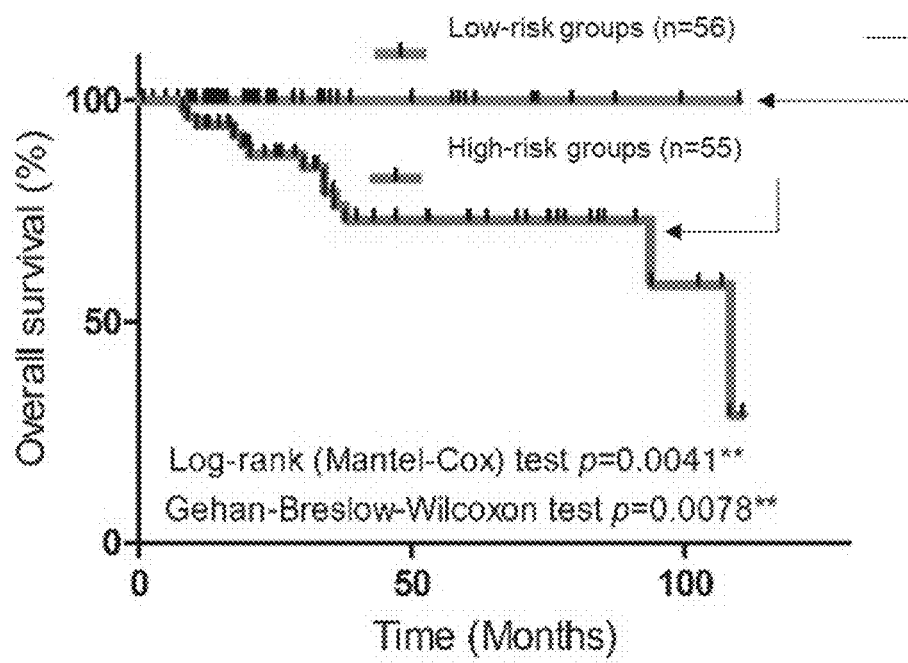
Figure 5E:
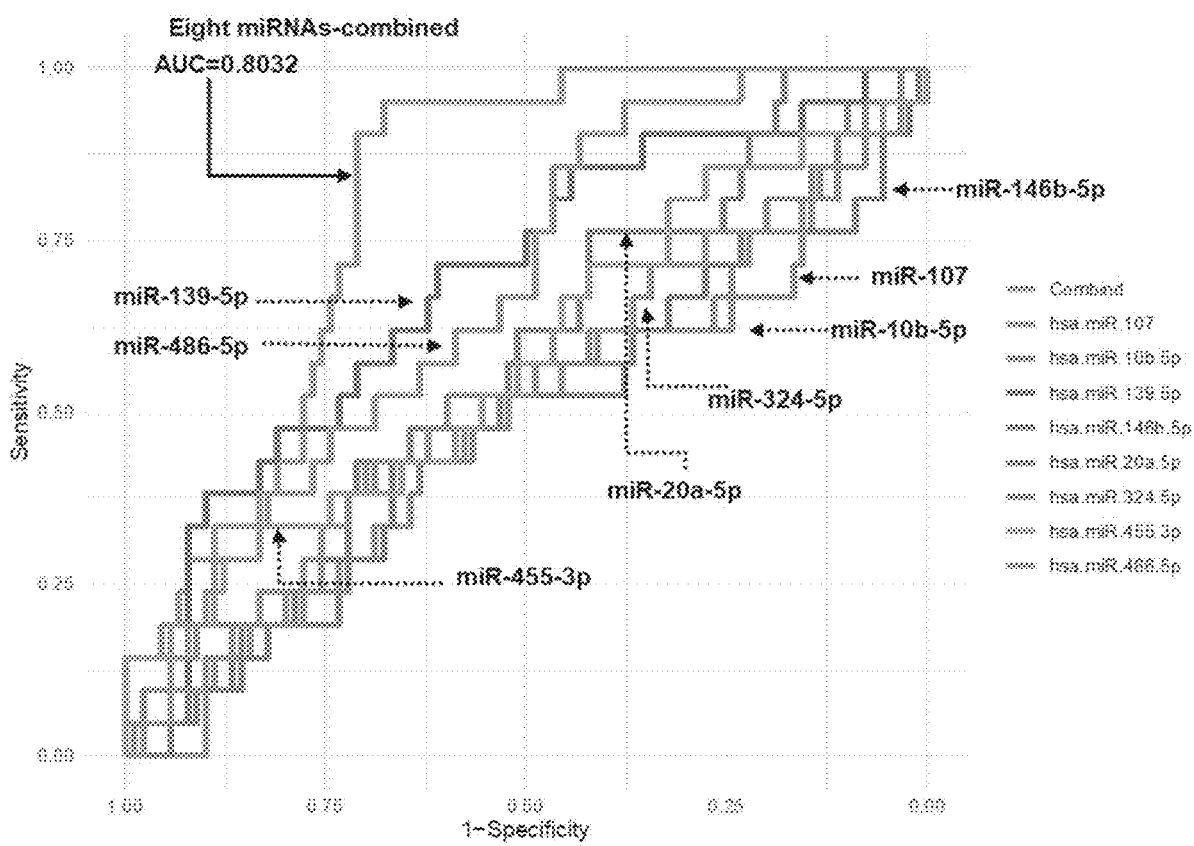

FIGS. 5A-5E show diagrams of the predictive values of the 8-miRNA signature in 111 TNBC patients. In FIG. 5A, the upper diagram is the 8-miRNA signature risk score distribution with DFS and OS status of patients. The middle and lower diagrams are the colorgrams of 8-miRNA expression profiles of high- and low-risk groups with TNBC. The central dotted line represents the median miRNA signature cutoff dividing patients into low- and high-risk groups. FIG. 5B shows the expression of heat-map in 8 miRNAs for 111 TNBC patients. FIG. 5C shows Kaplan-Meier estimates of the low- and high-risk groups in DFS for training set. FIG. 5D shows Kaplan-Meier estimates of the low- and high-risk groups in overall survival (OS) for training set. FIG. 5E shows ROC for TNBC recurrence by the miRNA signature between patients with or without recurrence in the combined or respectively miRNAs. In FIGS. 5A-5E, the abbreviation of OS stands for overall survival; the abbreviation of DFS stands for disease free survival; the abbreviation of R stands for recurrence; and the abbreviation of NR stands for non-recurrence.

From FIGS. 5A-5E, it can be known that the 8 combined miRNAs has the strongest predictive value than single miRNA. In FIGS. 5A and 5B, by dividing the risk score according to its median (median=1.602), 111 patients were stratified into the high-risk (n=55) and low-risk (n=56) groups (6 patients did not have OS or DFS data in the TCGA_TNBC dataset). Moreover, in FIGS. 5C and 5D, Kaplan-Meier survival analysis of the 8-miRNA signature was used to compare the high-risk group with the low-risk group regarding patient DFS and OS. In the analysis, it was confirmed that the high-risk group had a significantly higher recurrence and death rate. More significantly, the ROC curve further demonstrated that the risk score model was able to effectively predict the recurrence of TNBC patients. Additionally, the AUC value of the 8-miRNA signature was 0.8032 (see FIG. 5E).

These results further support that the combination of the 8-miRNA signature significantly improved the prognostic value. Patients in the high-risk group had a higher relapse and death probability than those in the low-risk group. The sequence of the 8 miRNAs are listed in Table 5 below.

TABLE 5

Sequence listing of the 8 miRNAs

| SEQ ID No | miRNA | Sequence of miRNA (5'- . . . -3') |
|---|---|---|
| 1 | hsa-miR-10b-5p | UACCCUGUAGAACCGAAUUUGUG |
| 2 | hsa-miR-139-5p | UCUACAGUGCACGUGUCUCCAGU |
| 3 | hsa-miR-486-5p | UCCUGUACUGAGCUGCCCCGAG |
| 4 | hsa-miR-455-3p | GCAGUCCAUGGGCAUAUACAC |
| 5 | hsa-miR-20a-5p | UAAAGUGCUUAUAGUGCAGGUAG |
| 6 | hsa-miR-107 | AGCAGCAUUGUACAGGGCUAUCA |
| 7 | hsa-miR-324-5p | CGCAUCCCCUAGGGCAUUGGUG |
| 8 | hsa-miR-146b-5p | UGAGAACUGAAUUCCAUAGGCUG |

Survival Analysis of the Prognostic miRNA Signature in TNBC

Figure 6A:
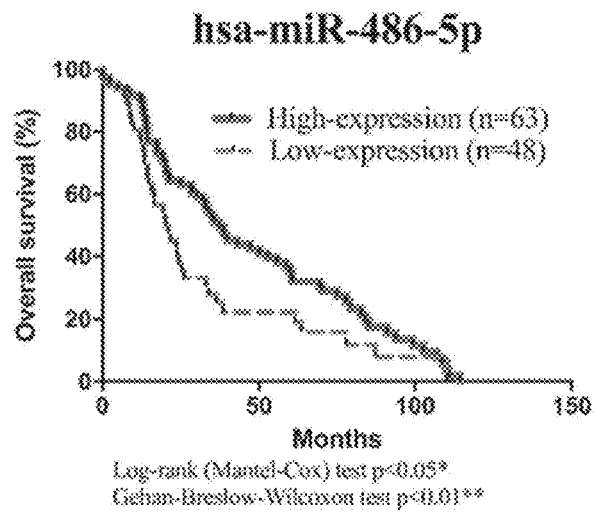
FIGS. 6A and 6B show the results of Kaplan-Meier survival analysis estimates overall survival (OS) of TNBC patients according to these 8 miRNAs expression.
Figure 6A:
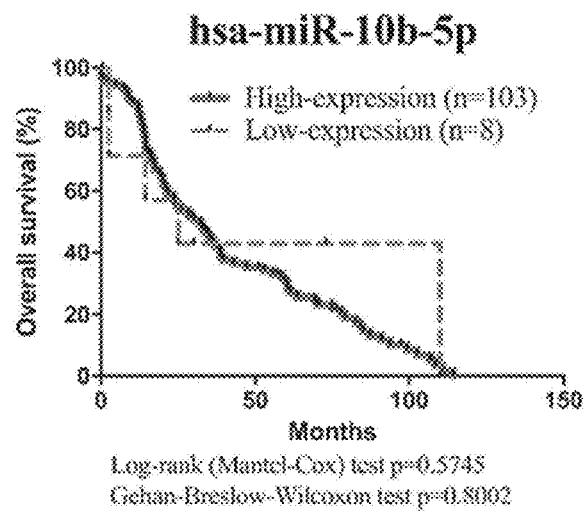
Figure 6A:
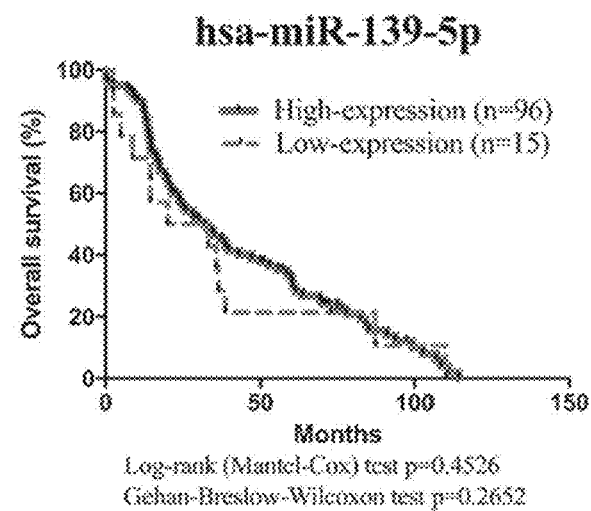
Figure 6B:
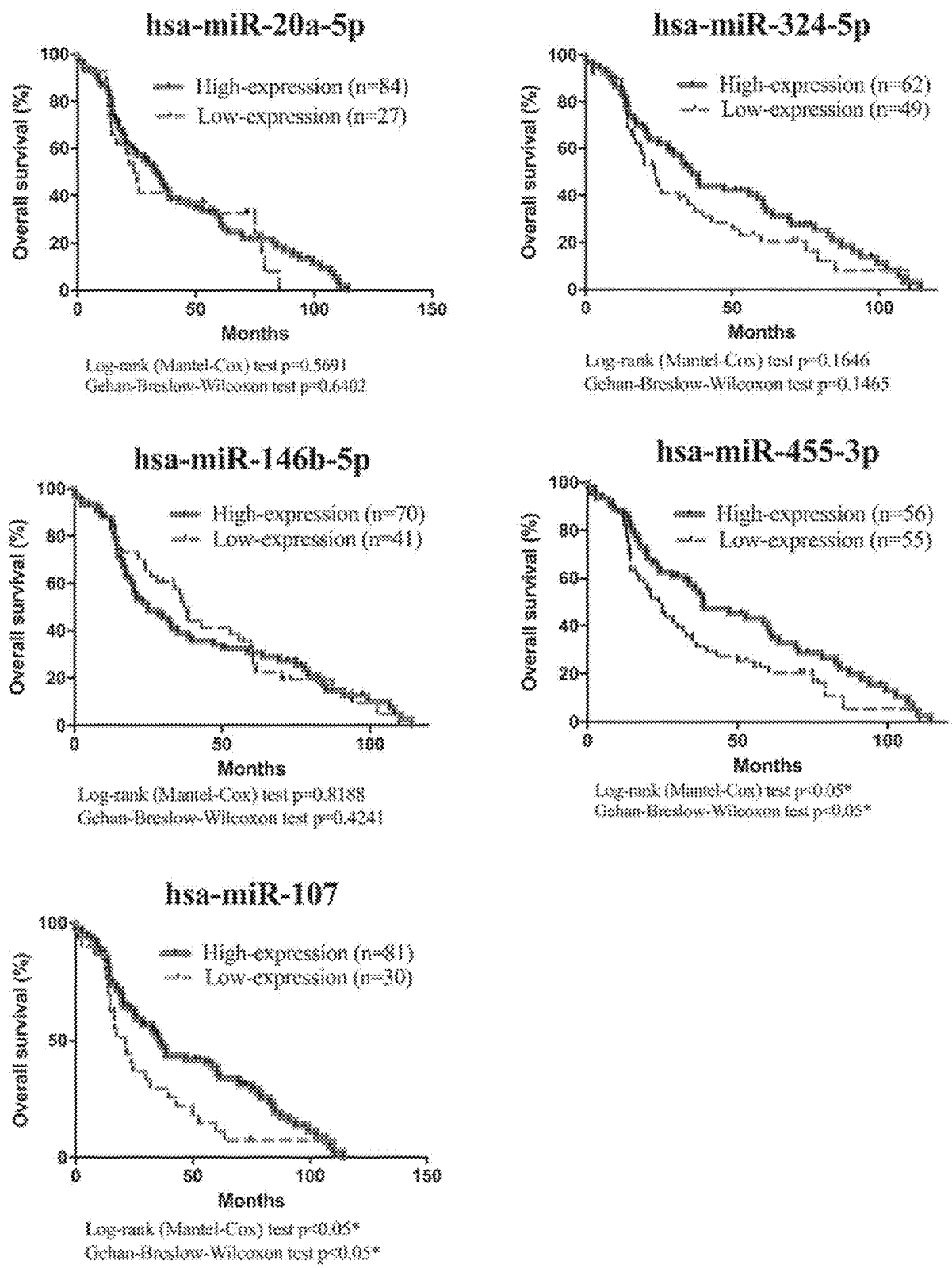

To further investigate the specific association of the 8 individual miRNAs with clinical characteristics regarding the OS and DFS of TNBC patients, a comprehensive survival analysis was performed with the Kaplan-Meier method. FIGS. 6A and 6B show the results of Kaplan-Meier survival analysis estimates overall survival (OS) of TNBC patients according to these 8 miRNAs expression. There were total of 111 patients in the validation set (TCGA_TNBC). In FIG. 6A, the three downregulated miRNAs of hsa-miR-486-5p is significant in OS of patients with TNBC. In FIG. 6B, the upregulated miRNAs of hsa-miR-455-3p and hsa-miR-107 are significant in OS of patients with TNBC. The p-values were calculated using Log-rank and Gehan-Breslow-Wilcoxon tests. *p<0.05. Accordingly, the results suggested that three miRNAs (hsa-miR-455-3p, hsa-miR-107 and hsa-miR-486-5p) were significantly associated with OS (p-value<0.05).

Figure 7A:
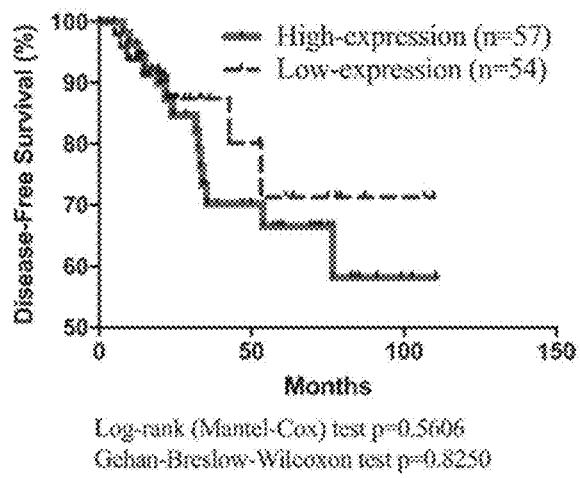
FIGS. 7A and 7B show the results of Kaplan-Meier survival analysis estimates disease free survival (DFS) of TNBC patients according to these 8 miRNAs expression.
Figure 7A:
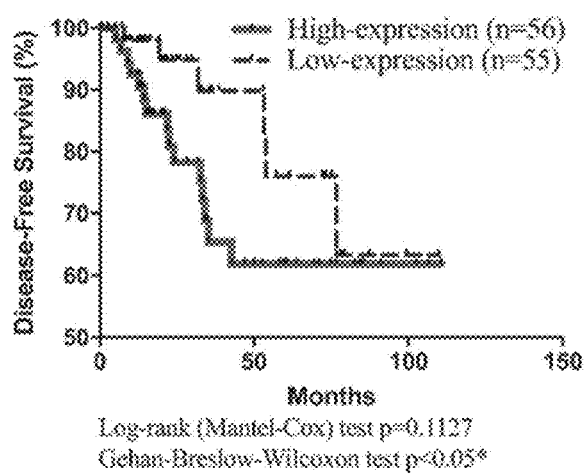
Figure 7A:
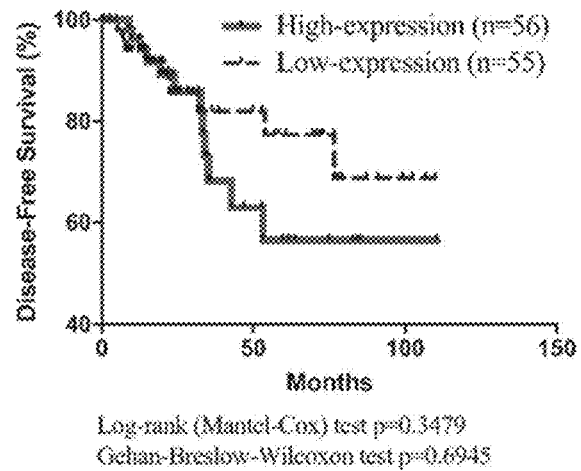
Figure 7B:
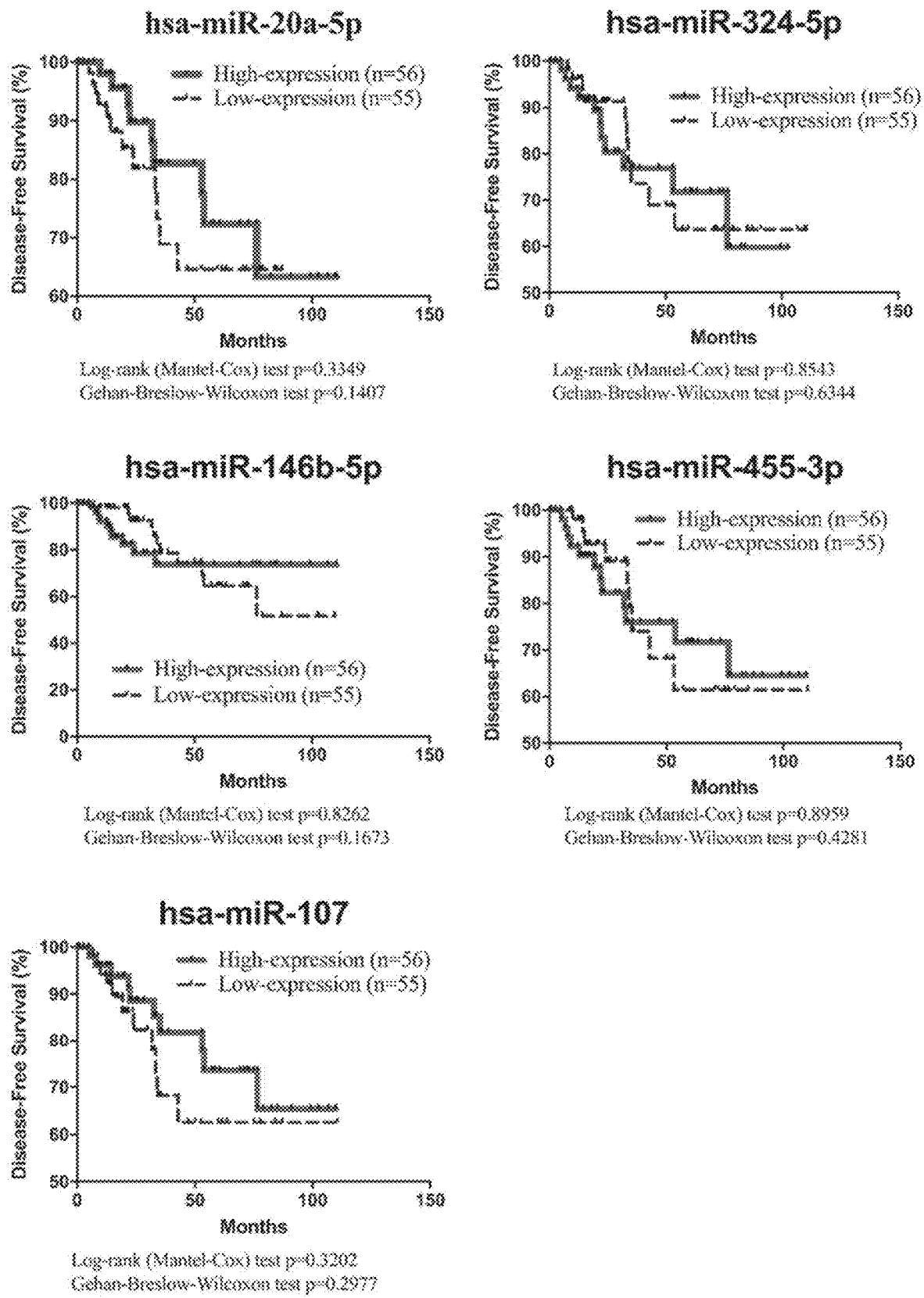

FIGS. 7A and 7B show the results of Kaplan-Meier survival analysis estimates disease free survival (DFS) of TNBC patients according to these 8 miRNAs expression. A total of 111 patients were included in the validation set (TCGA_TNBC). In FIG. 7A, hsa-miR-139-5p of the three downregulated miRNAs is significant in DFS of patients with TNBC. In FIG. 7B, all of the upregulated miRNAs are not significant in DFS of patients with TNBC. The p-values were calculated using Log-rank and Gehan-Breslow-Wilcoxon tests. *p<0.05. Accordingly, the DFS analysis results suggested that hsa-miR-139-5p was significantly associated with DFS (p-value<0.05). These results suggested that hsa-miR-139-5p was correlated with recurrence in TNBC patients. Nevertheless, hsa-miR-455-3p, hsa-miR-107 and hsa-miR-486-5p were associated with OS.

Figure 8A:
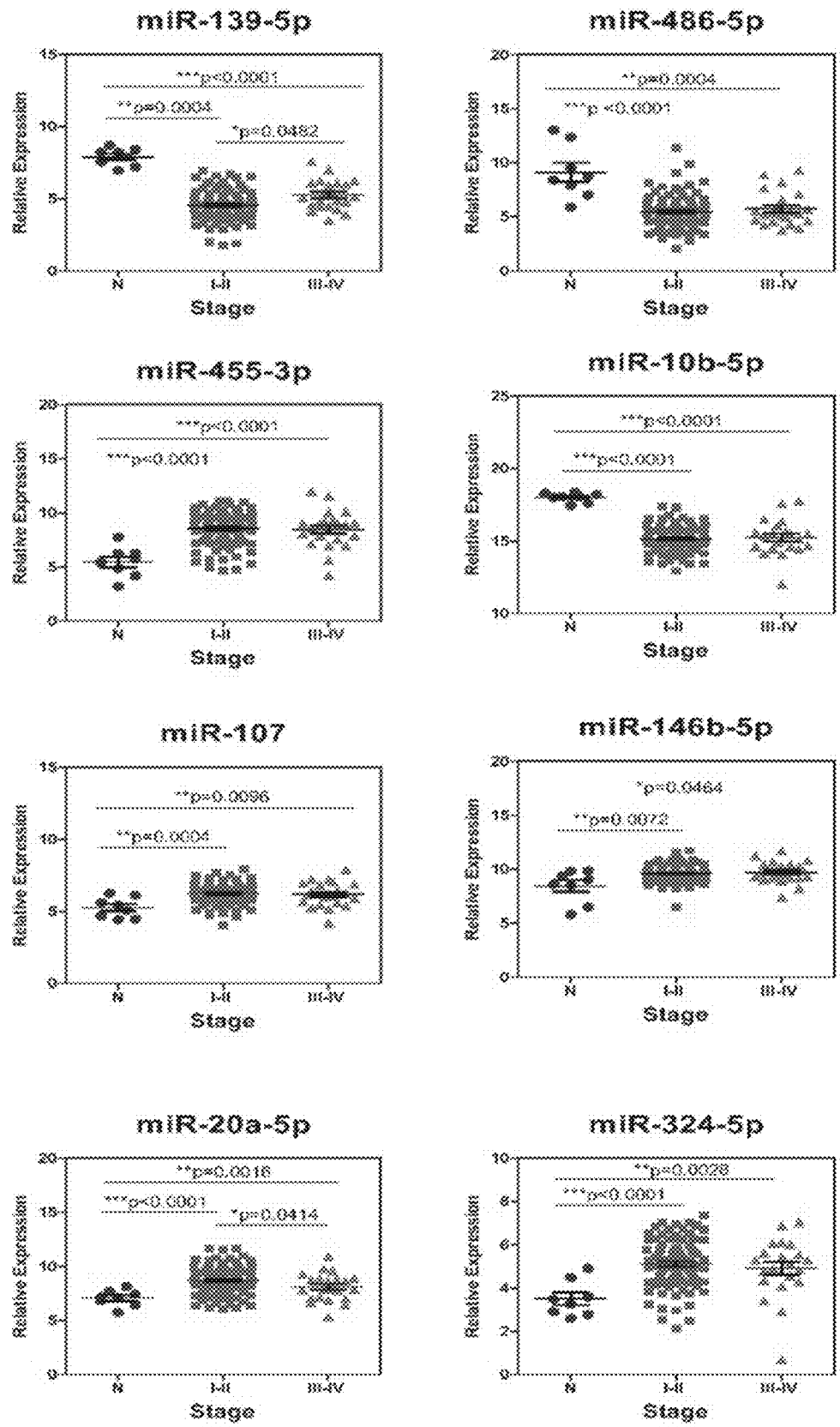
FIGS. 8A-8C show the difference in 8-signature miRNAs expression in subgroups divided by TNM Classification.
Figure 8B:
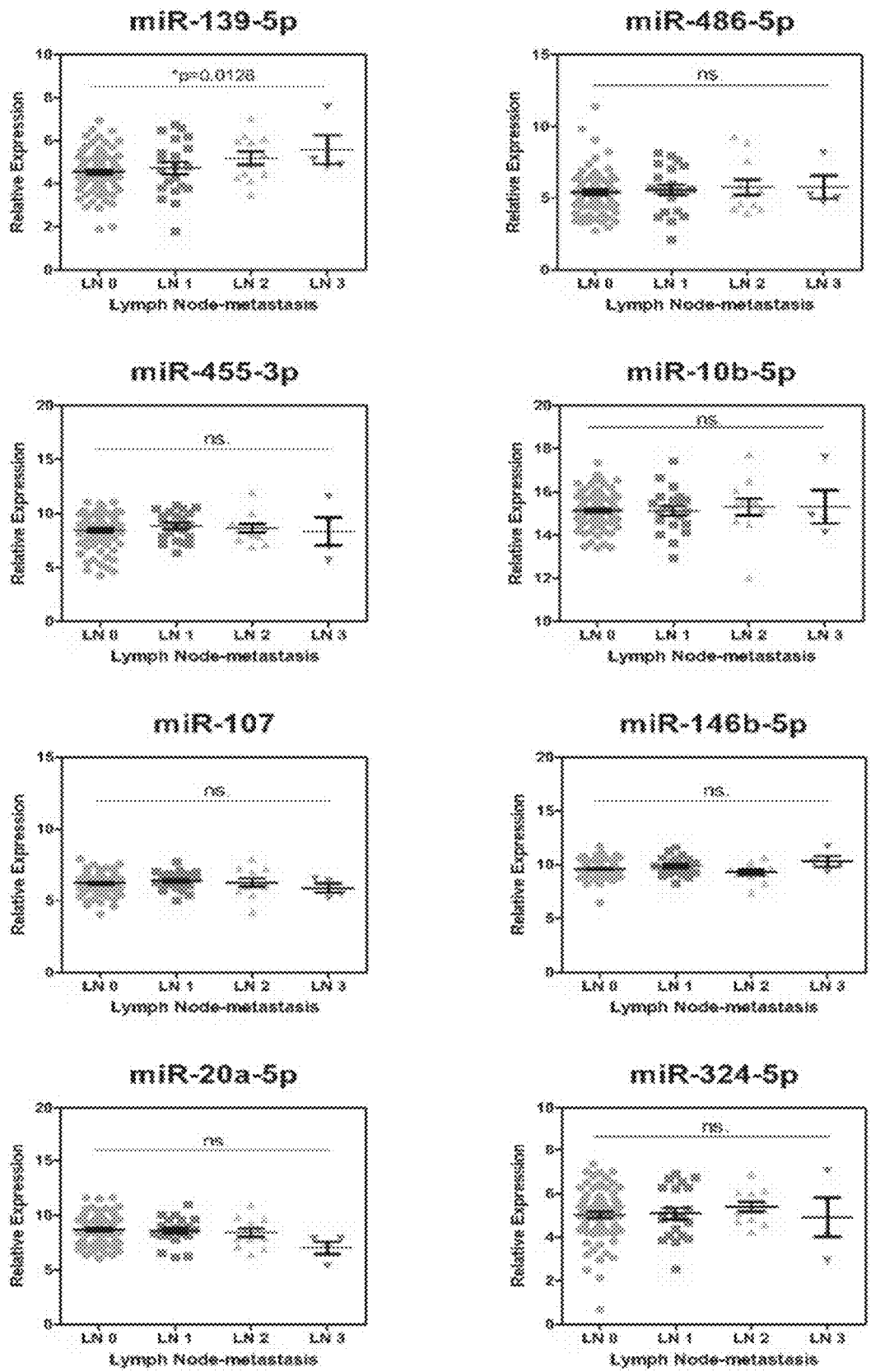
Figure 8C:
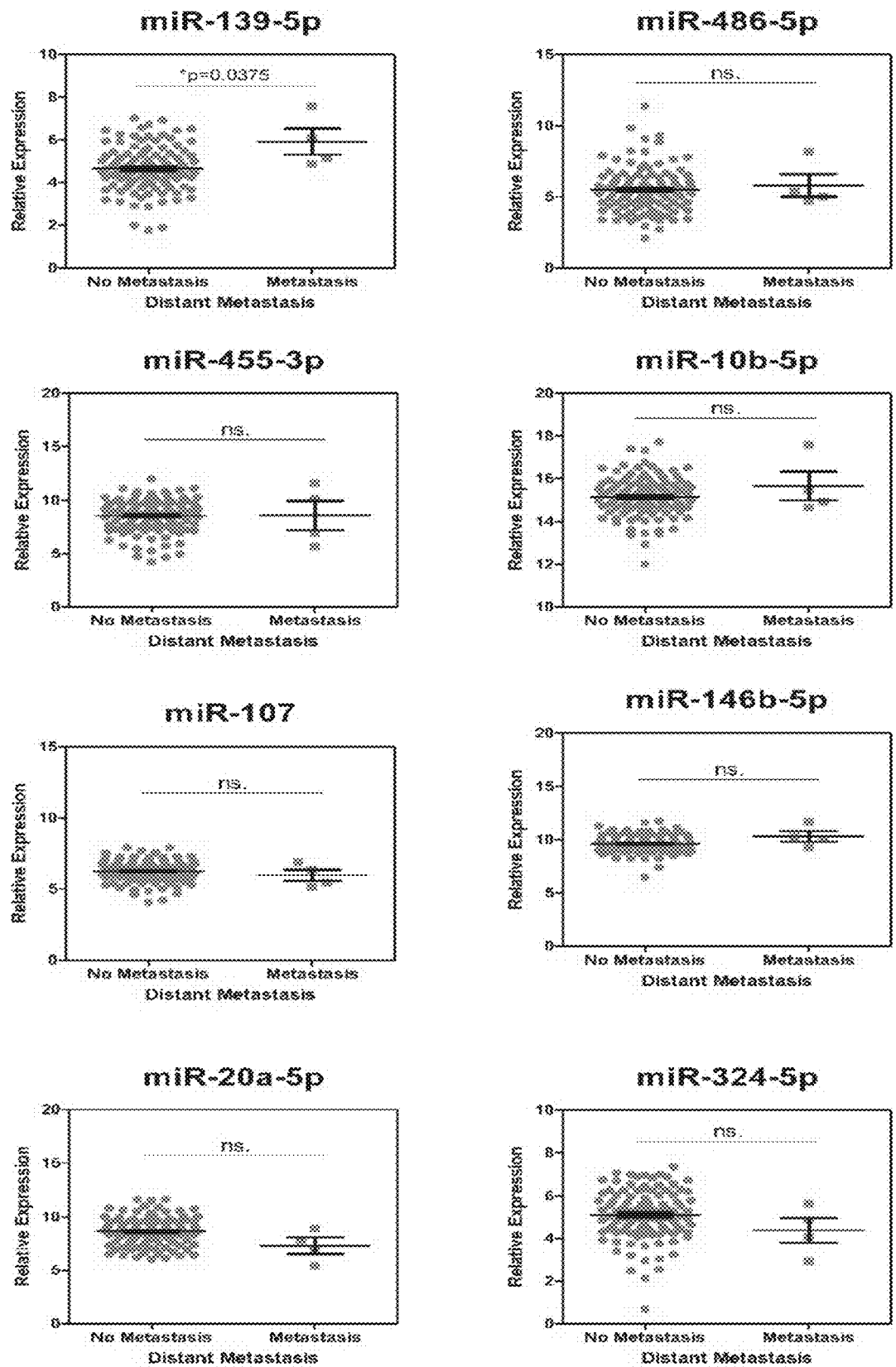

To investigate the main prognostic factors correlated with the TNM classification for diagnosis, tumor size, lymph node status and distant metastasis were used to represent the main prognostic factors. FIGS. 8A-8C show the difference in 8-signature miRNAs expression in subgroups divided by TNM Classification. In FIGS. 8A-8C, N stands for adjacent normal; T stands for tumor stage; LN stands for lymph node; M stands for Metastasis. FIG. 8A shows 111 TNBC patients, with 8 N vs. 89 stage I-II vs. 22 stage III-IV. The p-value were calculated with Kruskal-Wallis test. FIG. 8B shows 111 TNBC patients, with 74 LN0 vs. 21 LN1 vs. 12 LN2 vs. 4 LN3. The p-value were calculated with Kruskal-Wallis test. FIG. 8C shows 111 TNBC patients, with 107 no metastasis vs. 4 metastasis. The p-value were calculated with Mann-Whitney test. In FIG. 8A, only hsa-miR-139-5p was significantly expressed in tumor stages I-II (early stage) and III-IV (p-value<0.05). In FIGS. 8B-8C, it was also found that hsa-miR-139-5p was highly correlated with lymph node metastasis (p-value<0.05, FIG. 8B) and highly expressed in distant metastasis (p-value<0.05, FIG. 8C).

Figure 9A:
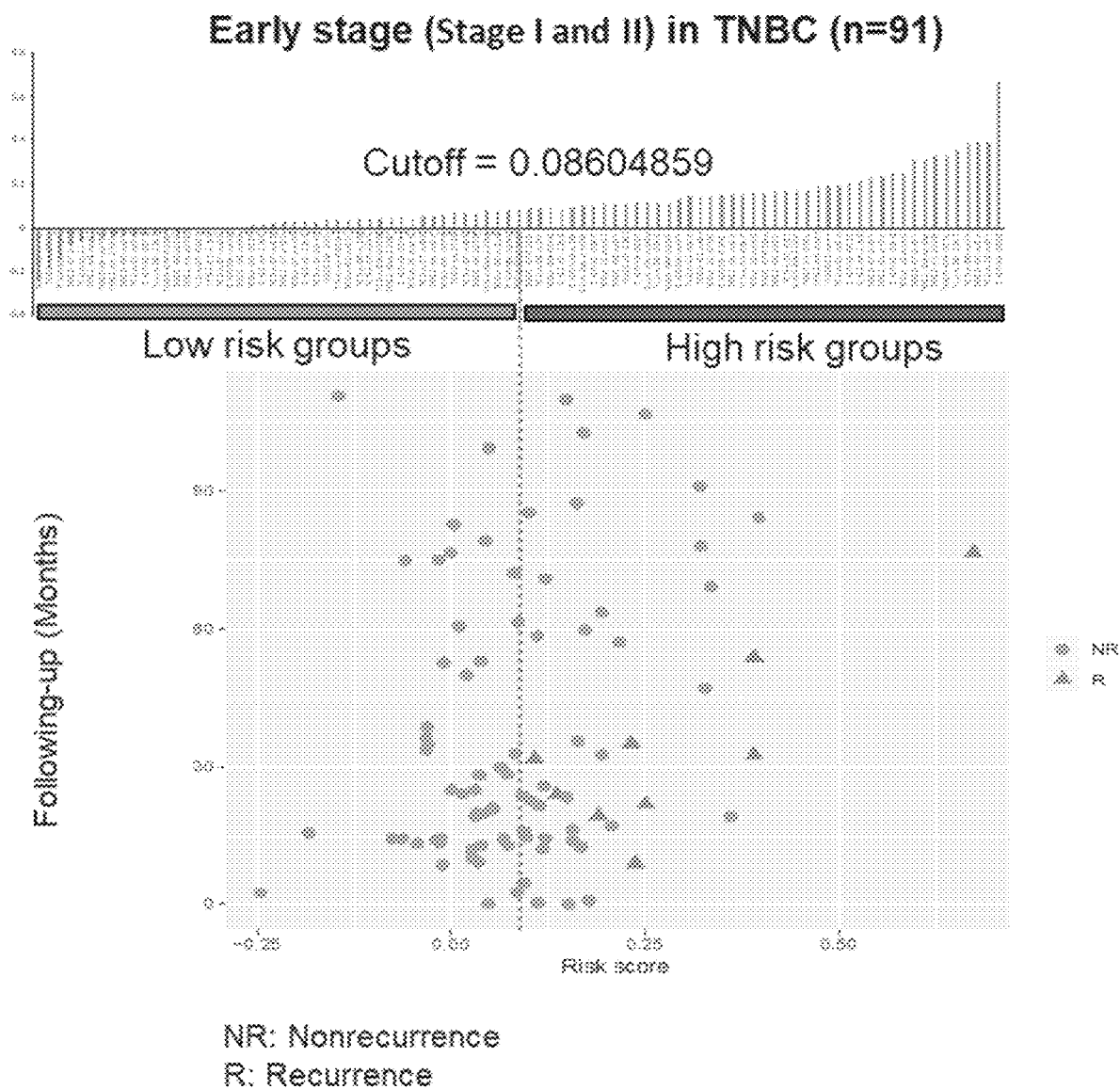
FIGS. 9A-9C show predictive value of the 8-miRNA signature for 91 patients with early-stage TNBC.
Figure 9B:
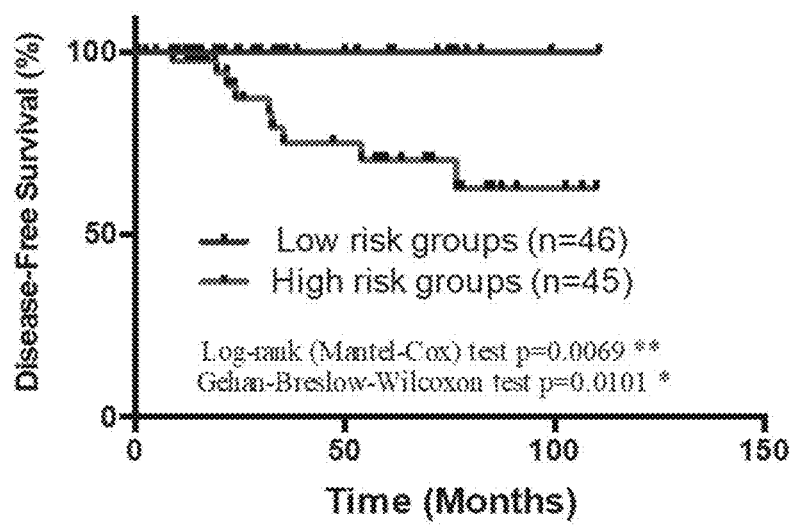
Figure 9C:
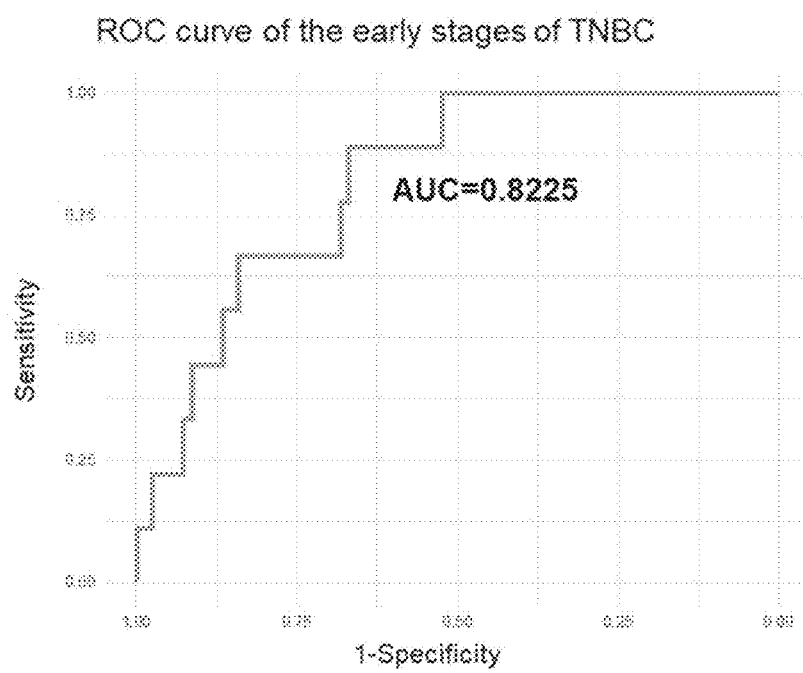

The 8-miRNA signature was assessed in the early stage of TNBC with the distribution of the 8-miRNA signature with risk scores and the recurrence status of the combined 91 patients (stage I and II) from the TCGA_TNBC dataset. Patients with high risk scores tended experience increased relapse compared with patients with low risk scores (AUC=0.8225; FIG. 9C). FIGS. 9A-9C show predictive value of the 8-miRNA signature for 91 patients with early-stage TNBC. FIG. 9A shows the 8-miRNA signature risk score distribution and patient DFS. In the colorgram, the middle vertical line represents the median miRNA signature cutoff dividing patients into low- and high-risk groups. FIG. 9B shows Kaplan-Meier estimates of DFS in the training set. FIG. 9C shows ROC for TNBC recurrence by the 8-miRNA signature between patients with recurrence and without recurrence in the combined or respective miRNAs. The 8 combined miRNAs had the strongest predictive value in the early stage.

As noted above, these results indicated that hsa-miR-139-5p may play an important role in the progression and metastasis of TNBC. The 8-miRNA signature is a predictor for the recurrence of patients in the early stage.

Figure 10A:
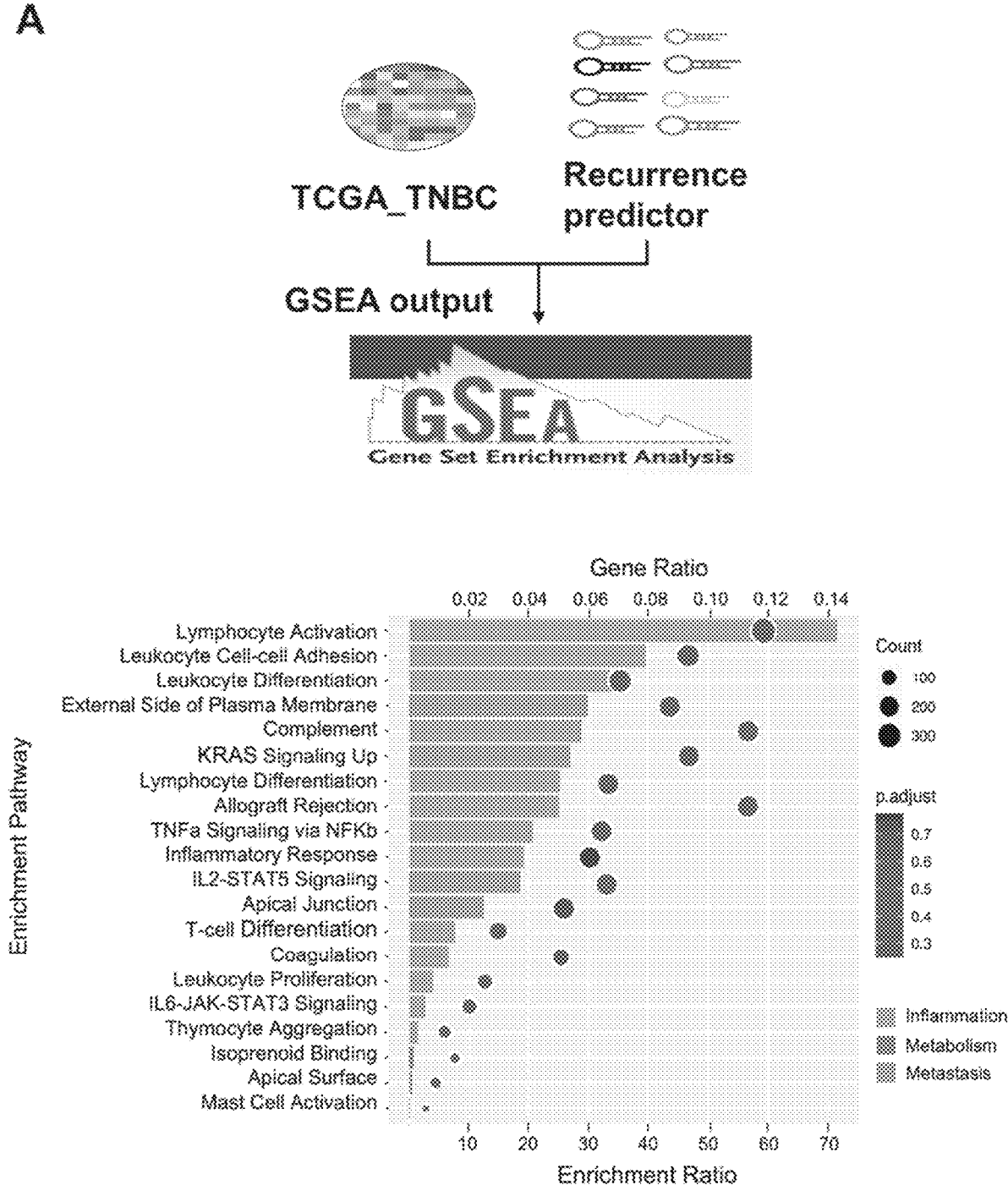
FIGS. 10A-10B show the network of enrichment analyzed for the 8-recurrence predictor of TNBC.
Figure 10B:
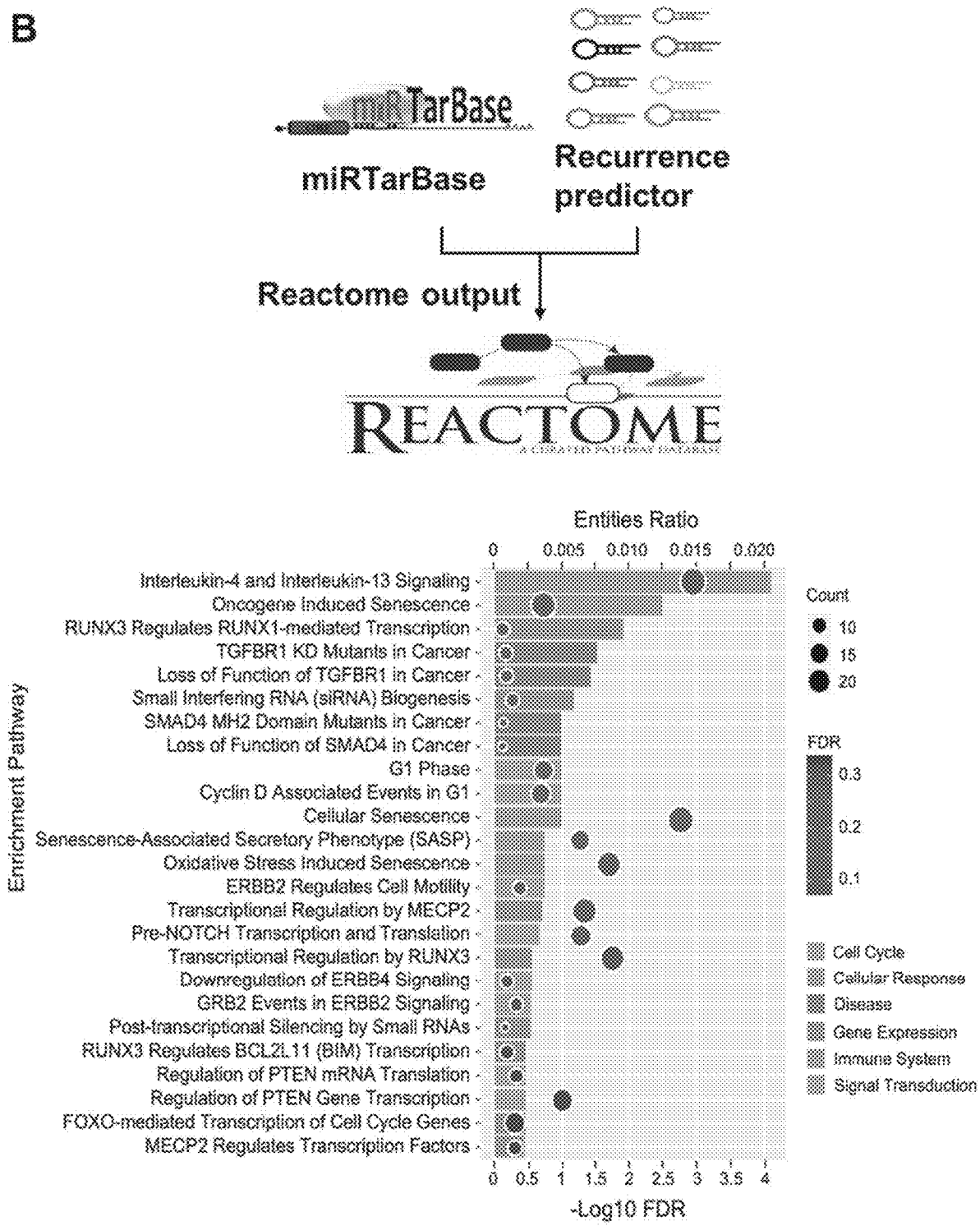

Identification of Gene Sets Enriched with the 8-miRNA Signature-Based Risk Score FIGS. 10A-10B show the network of enrichment analyzed for the 8-recurrence predictor of TNBC. Upper part of FIG. 10A shows the workflow of enriching the mRNA expression of TCGA_TNBC and 8-miRNA recurrence predictor with Gene Set Enrichment Analysis (GSEA). To comprehensively study the interaction between miRNAs and their functions, GO and Hallmark pathway analyses for the 8-miRNA signature were performed in the high-risk group.

Lower part of FIG. 10A is a bubble pattern showing top 20 of enrichment pathways with GeneRatio, gene count and p.adjust (FDR), and the inflammatory regulation and metastasis correlated with enrichment gene analysis. Functional enrichment analysis revealed that the 8-miRNA signature was enriched in inflammation, metastasis and metabolism, and the top 20 pathways are shown in Table 6 below.

TABLE 6

The annotation of 8 miRNAs in TNBC by previous experimental studies (UP: Upregulation; DOWN: Downregulation).

| Name | Functional role in TNBC | Expression level | Ref. |
|---|---|---|---|
| miR-139-5p | metastasis | DOWN | [1, 2] |
| miR-10b-5p | chemoresistance, metastasis | DOWN | [3-6] |
| miR-486-5p | immunomodulatory tumor suppressor | DOWN | [7-9] |
| miR-107 | metastasis, correlated with relapse | UP/DOWN | [6, 10-13] |
| miR-455-3p | migration, invasion | UP | [14] |
| miR-146b-5p | proliferation, homologous recombination | UP | [15] |
| miR-20a-5p | migration, invasion, growth | UP | [16, 17] |
| miR-324-5p | anti-apoptosis potential, associated with decreased OS | UP | [6, 18] |

1. Krishnan K, Steptoe A L, Martin H C, Pattabiraman D R, Nones K, Waddell N, et al. miR-139-5p is a regulator of metastatic pathways in breast cancer. RNA (New York, NY). 2013; 19: 1767-80.
2. Yang F, Zhang W, Shen Y, Guan X. Identification of dysregulated microRNAs in triple-negative breast cancer (review). Int J Oncol. 2015; 46: 927-32.
3. Fkih M'hamed I, Privat M, Trimeche M, Penault-Llorca F, Bignon Y J, Kenani A. miR-10b, miR-26a, miR-146a And miR-153 Expression in Triple Negative Vs Non Triple Negative Breast Cancer: Potential Biomarkers. Pathology oncology research : POR. 2017; 23: 815-27.
4. Gupta I, Sareyeldin R M, Al-Hashimi I, Al-Thawadi H A, Al Farsi H, Vranic S, et al. Triple Negative Breast Cancer Profile, from Gene to microRNA, in Relation to Ethnicity. Cancers (Basel). 2019; 11.
5. Ouyang M, Li Y, Ye S, Ma J, Lu L, Lv W, et al. MicroRNA profiling implies new markers of chemoresistance of triple-negative breast cancer. PloS one. 2014; 9: e96228.
6. Turashvili G, Lightbody E D, Tyryshkin K, SenGupta S K, Elliott B E, Madarnas Y, et al. Novel prognostic and predictive microRNA targets for triple-negative breast cancer. FASEB J. 2018: fj201800120R.
7. Abdallah R, Youness R, El Meckawy N, El Sebaaei A, Abdelmotaal A, Assal R. 88P Crosstalk between hesperetin and miR-486-5p in triple-negative breast cancer (TNBC): An approach towards precision medicine. Annals of Oncology. 2018; 29: mdy314. 028.
8. Abdallah R, Youness R, El Meckawy N, El Sebaei A, Abdelmotaal A, Assal R. Paradoxical effects of miR-486-5p on the oncogenic and immunogenic profiles in triple negative breast cancer (TNBC). European Journal of Cancer. 2018; 92: S123.
9. Elkhouly A, Youness R, Gad MJAoO. 172P miR-486-5p counteracts the shedding of MICA/B and CD155 immune-ligands in TNBC patients. 2019; 30: mdz450. 009.
10. Li X Y, Luo Q F, Wei C K, Li D F, Li J, Fang L. MiRNA-107 inhibits proliferation and migration by targeting CDK8 in breast cancer. International journal of clinical and experimental medicine. 2014; 7: 32-40.
11. Luo Z, Zheng Y, Zhang W. Pleiotropic functions of miR107 in cancer networks. OncoTargets and therapy. 2018; 11: 4113-24.
12. Shen S, Sun Q, Liang Z, Cui X, Ren X, Chen H, et al. A prognostic model of triple-negative breast cancer based on miR-27b-3p and node status. PLoS One. 2014; 9: e100664.
13. Zhang L, Ma P, Sun L M, Han Y C, Li B L, Mi X Y, et al. MiR-107 down-regulates SIAH1 expression in human breast cancer cells and silencing of miR-107 inhibits tumor growth in a nude mouse model of triple-negative breast cancer. Mol Carcinog. 2016; 55: 768-77.
14. Li Z, Meng Q, Pan A, Wu X, Cui J, Wang Y, et al. MicroRNA-455-3p promotes invasion and migration in triple negative breast cancer by targeting tumor suppressor EI24. Oncotarget. 2017; 8: 19455-66.
15. Garcia A I, Buisson M, Bertrand P, Rimokh R, Rouleau E, Lopez B S, et al. Down-regulation of BRCA1 expression by miR-146a and miR-146b-5p in triple negative sporadic breast cancers. EMBO molecular medicine. 2011; 3: 279-90.
16. Jin L, Lim M, Zhao S, Sano Y, Simone B A, Savage J E, et al. The metastatic potential of triple-negative breast cancer is decreased via caloric restriction-mediated reduction of the miR-17~92 cluster. Breast cancer research and treatment. 2014; 146: 41-50.
17. Li X, Wu B, Chen L, Ju Y, Li C, Meng S. Urokinase-type plasminogen activator receptor inhibits apoptosis in triple-negative breast cancer through miR-17/20a suppression of death receptors 4 and 5. Oncotarget. 2017; 8: 88645-57.
18. El Majzoub R, Fayyad-Kazan M, Nasr El Dine A, Makki R, Hamade E, Gree R, et al. A thiosemicarbazone derivative induces triple negative breast cancer cell apoptosis: possible role of miRNA-125a-5p and miRNA-181a-5p. Genes & genomics. 2019; 41: 1431-43.

Accordingly, the enrichment ratio, which is the normalized enrichment score (NES)×GeneRatio (enrichment gene count/total gene count), was calculated and then this ratio was ranked. The bubble chart in lower part of FIG. 10A shows that the 8-miRNA signature was correlated with TNF-α/NF-κB signaling, thymocyte aggregation, mast cell activation, T-cell differentiation, inflammatory response and cell-cell adhesion. Moreover, the top 10 sets from GSEA with Hallmark gene sets showed that most pathways and genes are critical for inflammatory regulation, and cancer metastasis was associated with a high-risk score. The top 10 GO pathway gene sets were also associated with lymphocyte activation, cell-cell adhesion, and the external side of the plasma membrane, which are essential for inflammation and tumor progression.

To further confirm which biofunctions are correlated with this 8-miRNA signature, another approach was used. Upper part of FIG. 10B shows the workflow of combining the miRTarBase with 8-miRNA candidates to be recurrence predictor and enriching the miRTarBase with REACTOME. Then, Reactome, which is a functional enrichment tool, was used to align the targets and their biofunctions.

Next, lower part of FIG. 10B is a bubble pattern showing the top 25 enrichment pathways with entities.ratio, entities.found (count) and entities.FDR. The results showed that the 8-miRNA signature was correlated with interleukin-4 and interleukin-13 signaling, cellular senescence, transcriptional regulation by RUNX3, transcriptional regulation by MECP2 and oxidative stress-induced senescence. Furthermore, the top 25 functional pathways were ranked with entities. The FDRs are shown in Table 7 below. The bar chart demonstrates that the gene sets involved in the immune system, cellular response, gene expression and disease were significantly enriched in pathways related to the eight-miRNA recurrence predictor.

TABLE 7

MiRTarBase and Reactome were analyzed with the 8-miRNA signature.

| Function | Pathway name | Entities found | Entities total | Entities ratio | Entities p-value | Entities FDR |
|---|---|---|---|---|---|---|
| Immune system | Interleukin-4 and Interleukin-13 signaling | 21 | 211 | 0.014906394 | 5.64E−08 | 7.73E−05 |
| Cellular response | Oncogene-induced senescence | 13 | 42 | 0.002967149 | 4.76E−06 | 0.003262839 |
| Gene expression | RUNX3 regulates RUNX1-mediated transcription | 3 | 4 | 2.83E−04 | 2.65E−05 | 0.012106852 |
| Disease | TGFBR1 KD mutants in cancer | 3 | 6 | 4.24E−04 | 8.76E−05 | 0.029961642 |
| Disease | Loss of function of TGFBR1 in cancer | 3 | 7 | 4.95E−04 | 1.38E−04 | 0.037732025 |
| Gene expression | Small interfering RNA (siRNA) biogenesis | 3 | 9 | 6.36E−04 | 2.87E−04 | 0.065387672 |
| Cellular response | Cellular senescence | 21 | 198 | 0.01398799 | 6.56E−04 | 0.102699039 |
| Cell cycle | G1 phase | 8 | 48 | 0.003391028 | 6.84E−04 | 0.102699039 |
| Cell cycle | Cyclin D associated events in G1 | 8 | 48 | 0.003391028 | 6.84E−04 | 0.102699039 |
| Disease | SMAD4 MH2 domain mutants in cancer | 2 | 3 | 2.12E−04 | 8.28E−04 | 0.102699039 |
| Disease | Loss of function of SMAD4 in cancer | 2 | 3 | 2.12E−04 | 8.28E−04 | 0.102699039 |
| Cellular response | Oxidative stress-induced senescence | 13 | 114 | 0.008053691 | 0.00168596 | 0.179245562 |
| Cellular response | Senescence-associated secretory phenotype | 8 | 89 | 0.006287531 | 0.001825798 | 0.179245562 |
| Signal transduction | ERBB2 regulates cell motility | 4 | 19 | 0.001342282 | 0.001847892 | 0.179245562 |
| Gene expression | Transcriptional regulation by MECP2 | 15 | 100 | 0.007064641 | 0.00218222 | 0.198581976 |
| Signal transduction | Pre-NOTCH transcription and translation | 10 | 89 | 0.006287531 | 0.002535926 | 0.215553748 |
| Gene expression | Transcriptional regulation by RUNX3 | 15 | 118 | 0.008336277 | 0.003617939 | 0.279122234 |
| Signal transduction | Downregulation of ERBB4 signaling | 3 | 10 | 7.06E−04 | 0.003672661 | 0.279122234 |
| Signal transduction | GRB2 events in ERBB2 signaling | 4 | 20 | 0.001412928 | 0.004010608 | 0.288763746 |
| Gene expression | Posttranscriptional silencing by small RNAs | 2 | 7 | 4.95E−04 | 0.004348557 | 0.29570188 |
| Gene expression | RUNX3 regulates BCL2L11 (BIM) transcription | 4 | 6 | 4.24E−04 | 0.005365206 | 0.3421185 |
| Signal transduction | Regulation of PTEN mRNA translation | 4 | 29 | 0.002048746 | 0.005746118 | 0.3421185 |
| Signal transduction | Regulation of PTEN gene transcription | 8 | 70 | 0.004945249 | 0.005798619 | 0.3421185 |
| Gene expression | FOXO-mediated transcription of cell cycle genes | 8 | 27 | 0.001907453 | 0.006153079 | 0.350725501 |
| Gene expression | MECP2 regulates transcription factors | 4 | 10 | 7.06E−04 | 0.006561133 | 0.354301187 |

These results suggested that the 8-miRNA signature is most involved in inflammation and cancer metastasis. This finding might be due to immune escape to promote tumor recurrence, which consequently might have significantly contributed to patients with high risk scores having higher relapse and death rates. Therefore, this 8-miRNA signature is defined as the 8-miRNA recurrence predictor of TNBC in this study.

Validation of the miRNA Signature for TNBC Recurrence Prediction by the Validation Set To validate the prognostic role of this 8-miRNA signature, the same miRNA signature obtained from testing was applied to an additional 60 TNBC patients in independent cohorts. The expression in the validation cohort GSE40049, GSE19783 and E-MTAB-1989 datasets was assessed and comprised of recurrence events and no recurrence events. The clinicopathological characteristics are shown in Table 8 below.

TABLE 8

The clinicopathological characteristics of TNBC patients in the GSE40049, GSE19783 and E-MTAB-1989 datasets for the testing study.

| Dataset | GSE40049 | GSE19783 | E-MTAB-1989 |
|---|---|---|---|
| Number | | | |
| TNBC | 24 | 18 | 18 |
| Normal | 14 | 0 | 0 |
| Total | 38 | 18 | 18 |
| Age (years) | 55.52 | NA | 54 |
| Preservation type | Fresh tissue | Fresh tissue | FFPE |
| Tumor size | | NA | NA |
| T1-T2 | 23 | — | — |
| T3-T4 | 1 | — | — |
| Lymph node metastasis | | NA | NA |
| Present | 5 | — | — |
| Absent | 19 | — | — |
| Number of recurrence events | 7 | 7 | 10 |
| Median recurrence (years) | 5.1 | 6.8 | 2.4 |
| Platform | Applied Biosystems SOLiD sequencing | Agilent-019118 Human miRNA Microarray 2.0 | A-AFFY-184 - Affymetrix GeneChip miRNA 2.0 Array [miRNA-2_0] |

Figure 11A:
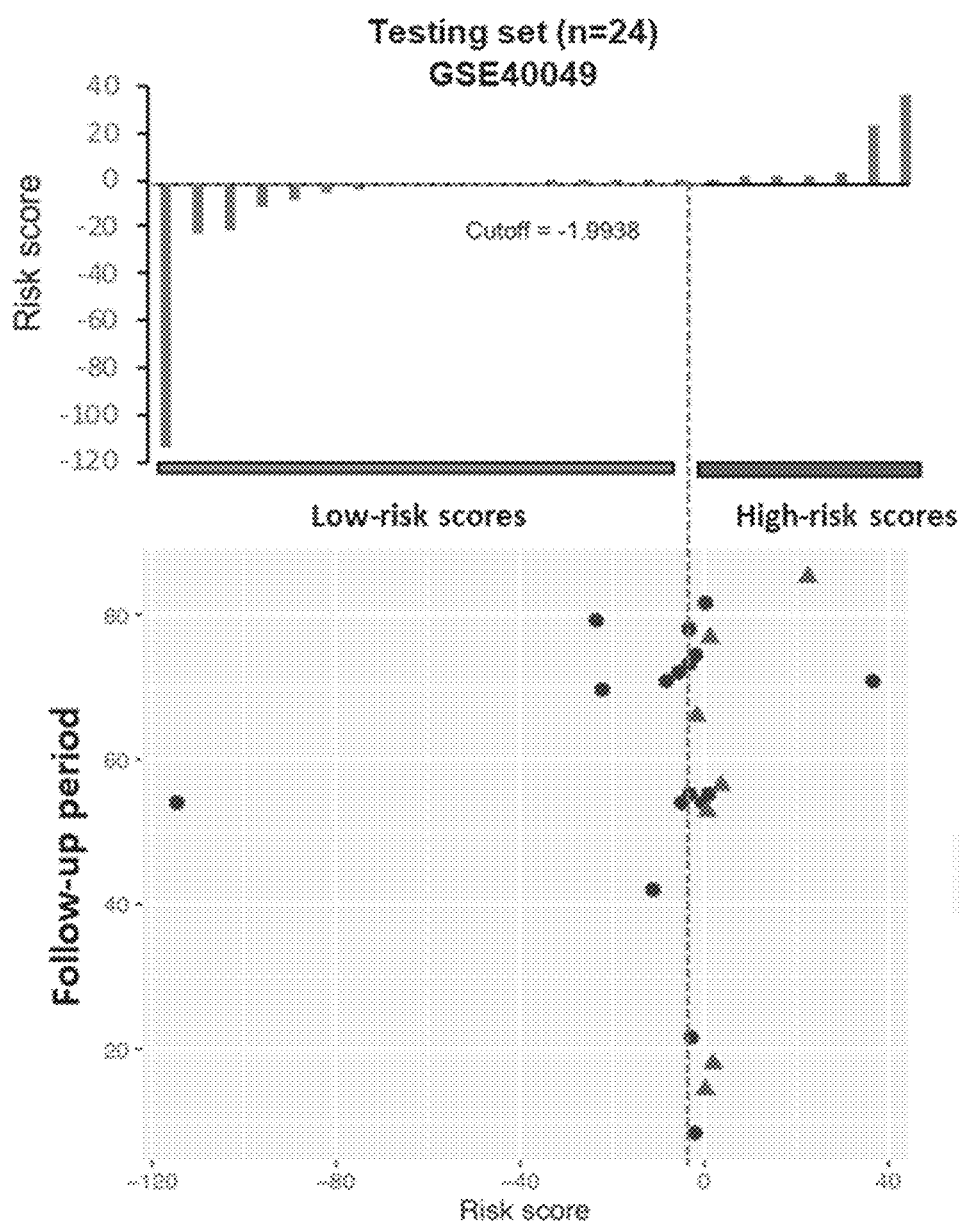
FIGS. 11A-11E show predictive value of the 8-miRNA signature for TNBC in testing study.

Logistic regression analysis using the same 8-miRNA signature was performed to diagnose and predict the probability of patient recurrence. FIGS. 11A-11E show predictive value of the 8-miRNA signature for TNBC in testing study. FIG. 11A shows the 8-miRNA signature risk score distribution with DFS status of patients. In FIG. 11A, the lower diagram is the colorgram of 8-miRNA expression profiles of high- and low-risk groups with TNBC. The dash line represents the median miRNA signature cutoff dividing patients into low- and high-risk groups in GSE40049. According to the median risk score (median=−1.9938), 24 patients were stratified into high-risk (n=11) and low-risk (n=13) groups in GSE40049.

Figure 11B:
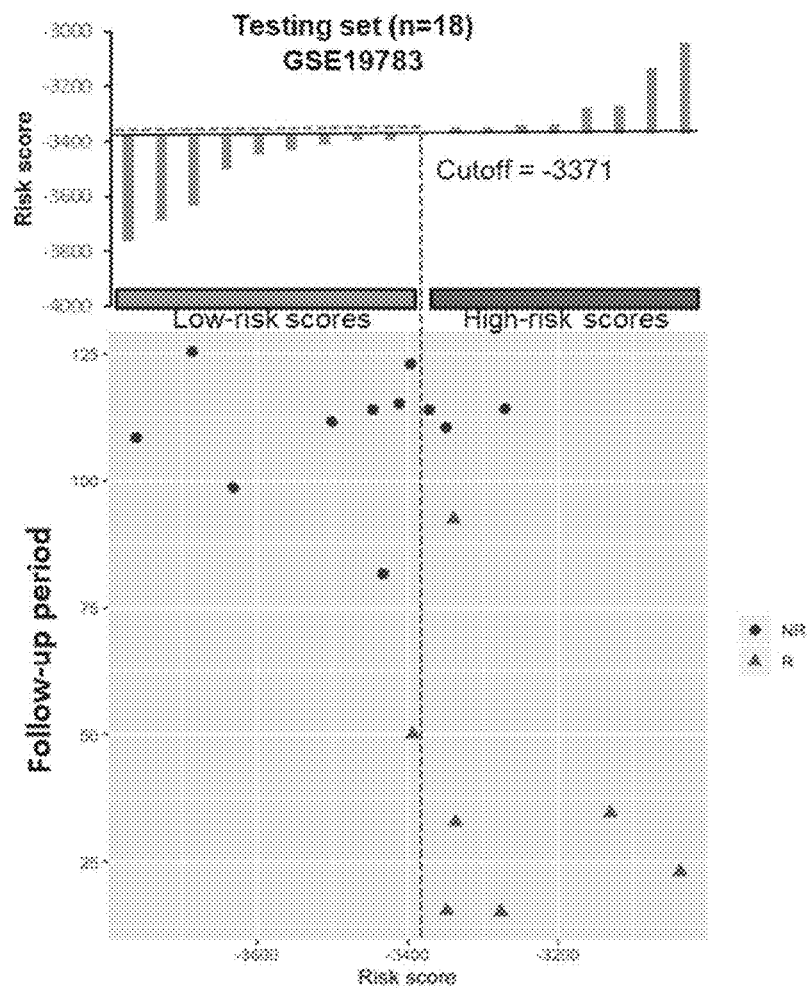

FIG. 11B shows the 8-miRNA signature risk score distribution with DFS status of patients. The color-gram of 8-miRNA expression profiles of high- and low-risk groups with TNBC. The dash line represents the median miRNA signature cutoff dividing patients into low- and high-risk groups in GSE19783. According to the median risk score (median=−3371), 18 patients were stratified into high-risk (n=8) and low-risk (n=10) groups in GSE19783.

Figure 11C:
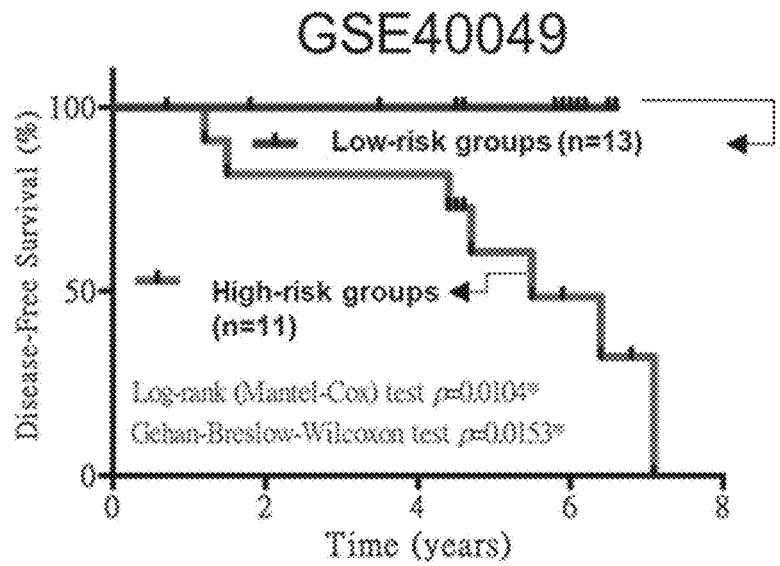
Figure 11D:
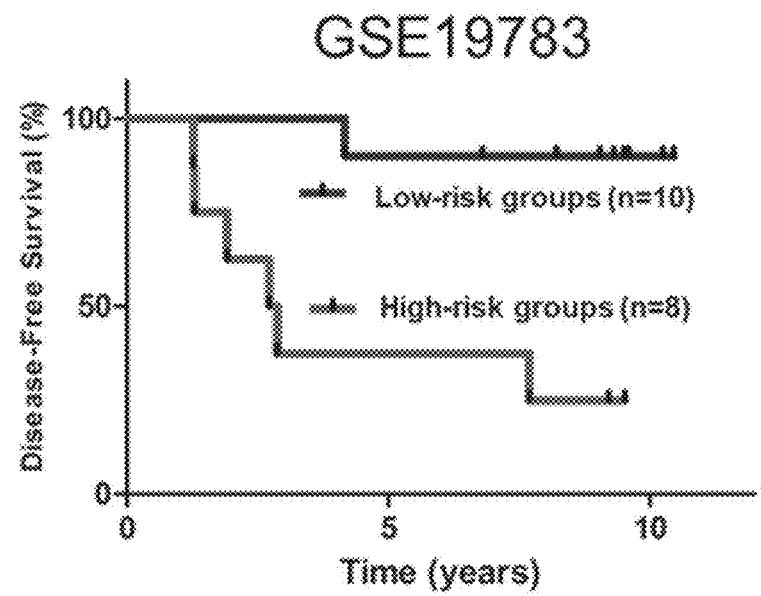

FIGS. 11C and 11D show Kaplan-Meier estimates of the low- and high-risk groups in DFS for testing set, GSE40049 and GSE19783, respectively. The Kaplan-Meier survival analysis with the 8-miRNA signature was used to compare the DFS of patients in the high-risk and low-risk groups. In the analysis, the 8-miRNA signature in the high-risk group was associated with a significantly higher recurrence in patients from the GSE40049, GSE19783, and E-MTAB-1989 (data not shown) datasets.

Figure 11E:
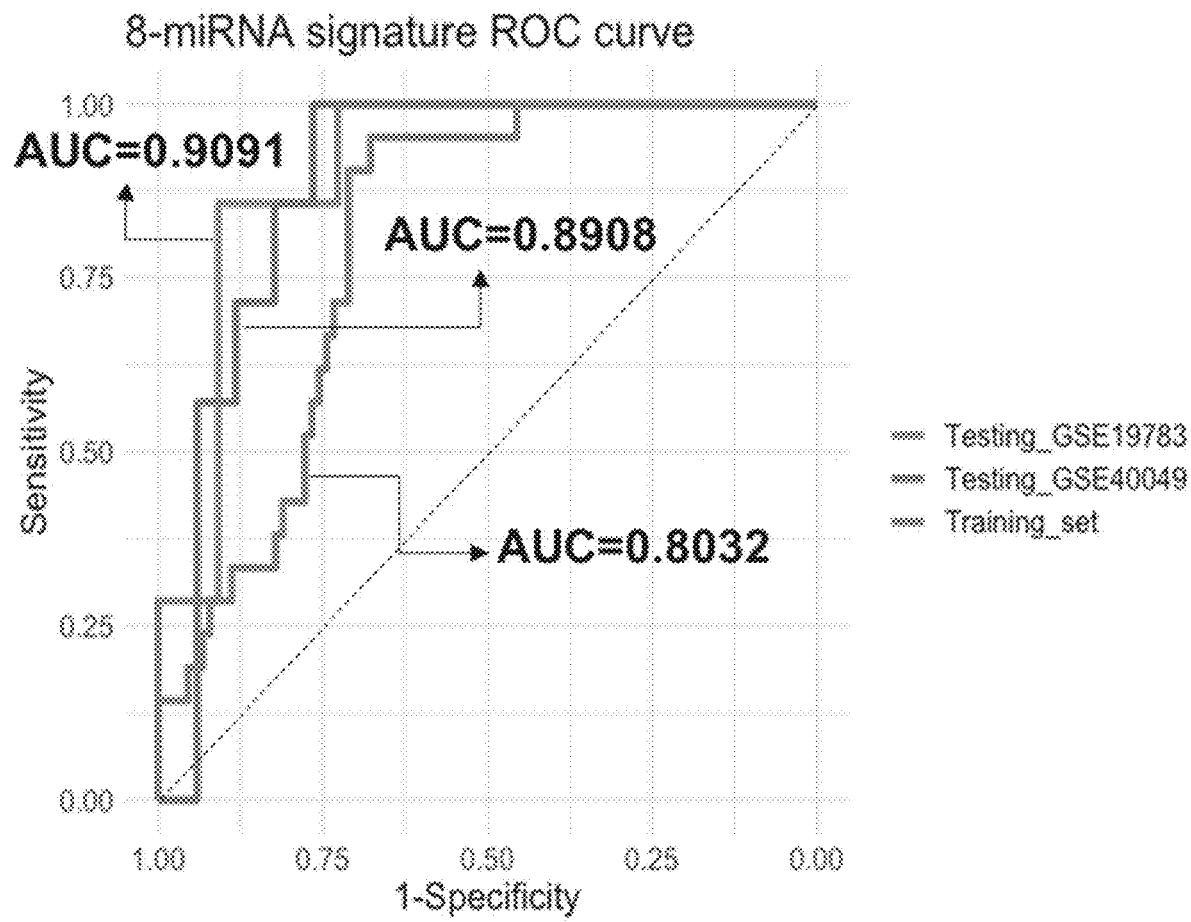

FIG. 11E shows ROC for TNBC patients relapse by the 8-miRNA signature between with/without recurrence in the combined or respectively miRNAs. The AUC support that the 8-miRNA signature have best predict no matter in training set (TCGA_TNBC) or testing sets (GSE40049 and GSE19783). The AUC values have been analyzed between the training and validation sets, which were 0.8961 and 0.9062 in the validation sets compared to 0.8032 in the training set. Hence, the ROC curve showed that the 8-miRNA signature in the validation set was better than that in the training set.

Accordingly, the combination of the 8-miRNA signature in the validation sets showed a significantly improved the prognostic value (AUC=0.8961 and 0.9062). Patients in the high-risk groups had more recurrence and death than those in the low-risk groups.

Discussion

A total of 8 miRNAs was identified as a signature that is associated with tumor recurrence in TNBC patients from the training set, TCGA_TNBC and GEOD-40525. These findings were consistent in three validation sets, GSE40049, GSE19783 and E-MTAB-1989. The prognostic risk score of recurrence in TNBC patients and individual current prognosis regimens based on precise predictions are important. The above results showed that patients with high risk scores according to this 8-miRNA signature have increased cancer relapse and decreased survival. In addition, previous studies have reported that these miRNAs are correlated with several cancer types, including colorectal cancer, breast cancer, lung cancer, gastric cancer, prostate cancer, endometrial cancer, pancreatic cancer, etc. These tumor-associated miRNAs may play a crucial role in the pathogenesis, tumor progression and prognosis of TNBC [30-34].

The World Health Organization (WHO) successfully separates breast cancer into TNBC and non-TNBC according to histopathologic characteristics [35]. The expression levels of 10 miRNAs in TNBC and non-TNBC were explored and compared to corresponding levels in adjacent normal tissues. First, the 10 miRNAs were significantly expressed between the two analyzed TNBC and non-TNBC groups. Second, the expression levels were very different between the TNBC and non-TNBC groups for miR (the p-value of 0.2137). Furthermore, based on the above findings, an 8-miRNA signature given by hsa-miR-139-5p, hsa-miR-107, hsa-miR-486-5p, hsa-miR-10b-5p, hsa-miR-146b-5p, hsa-miR-455-3p, hsa-miR-20a-5p and hsa-miR-324-5p expression levels was demonstrated to significantly influence the prognosis of TNBC patients but not non-TNBC patients.

In this study, the 8 miRNAs can predict the relapse of TNBC in the combination of logistic regression. For individuals, each miRNA also regulates the progression of TNBC in previous experimental studies by upregulation or downregulation of expression levels. Among them, 5 miRNAs upregulated in TNBC improve the metastasis progression of TNBC (such as hsa-miR-107, hsa-miR-20a-5p, and hsa-miR-455-3p), proliferation (such as miR146b-5p and hsa-miR-455-3p), and apoptosis (such as hsa-miR-20a-5p and hsa-miR-324-5p). The downregulated miRNAs were hsa-miR-139-5p, hsa-miR-10b-5p, and hsa-miR-486-5p, which are involved in chemoresistance and metastasis.

These miRNAs are involved in the complex regulation of TNBC progression, and most of them are associated with metastasis and resistance. Even though all of them are related to TNBC development, it is still difficult to determine the fate of cancer development based on each miRNA. Due to the complexity of the genetic network, tumor progression is more likely to depend on a group of critical miRNAs rather than a single one. Therefore, the prognosis analysis might not always be consistent with the unique miRNA expression level (FIGS. 6A-6B and 7A-7B). The evident reason is that miRNAs play a pleiotropic role in cancer. Some studies have indicated the pleiotropic role of miRNAs in various cancers, such as hsa-miR-107 and hsa-miR-146-5p. For TNBC, hsa-miR-107 regulates tumor progression by both oncogenic and suppressor effects on metastasis. These studies implied that relapse prediction might depend on a group of critical miRNAs, and this hypothesis was verified by the significant association of OS analyses in this study (FIGS. 5A-5E and 10A-10E).

Figure 12A:
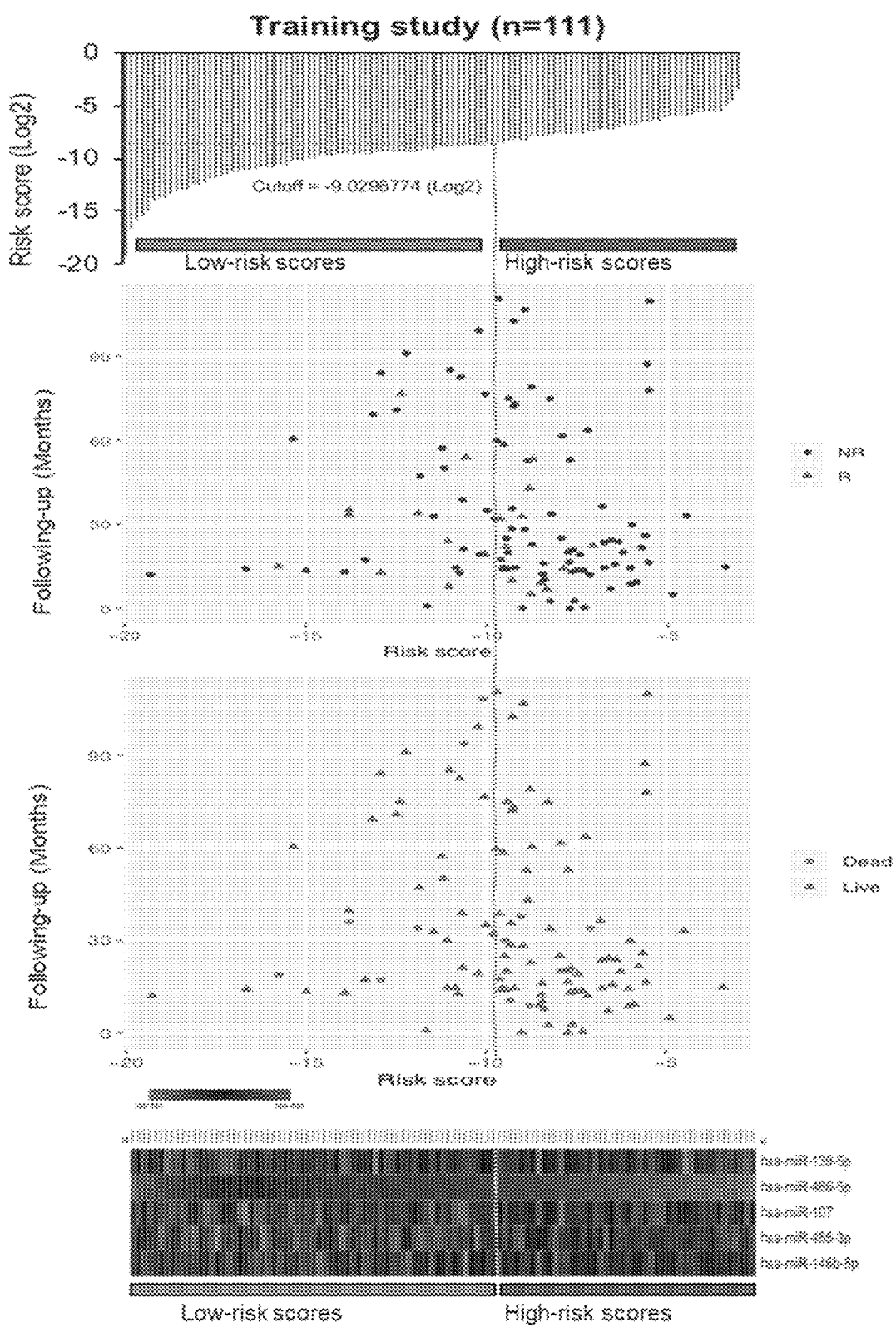
FIGS. 12A-12D show predictive value of the 5-miRNA signature for 111 TNBC patients.
Figure 12B:
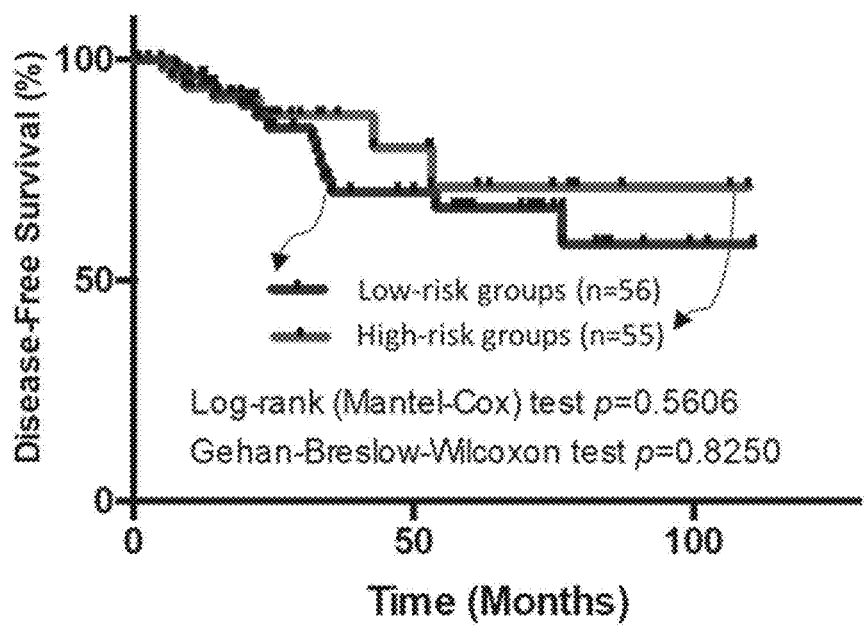
Figure 12C:
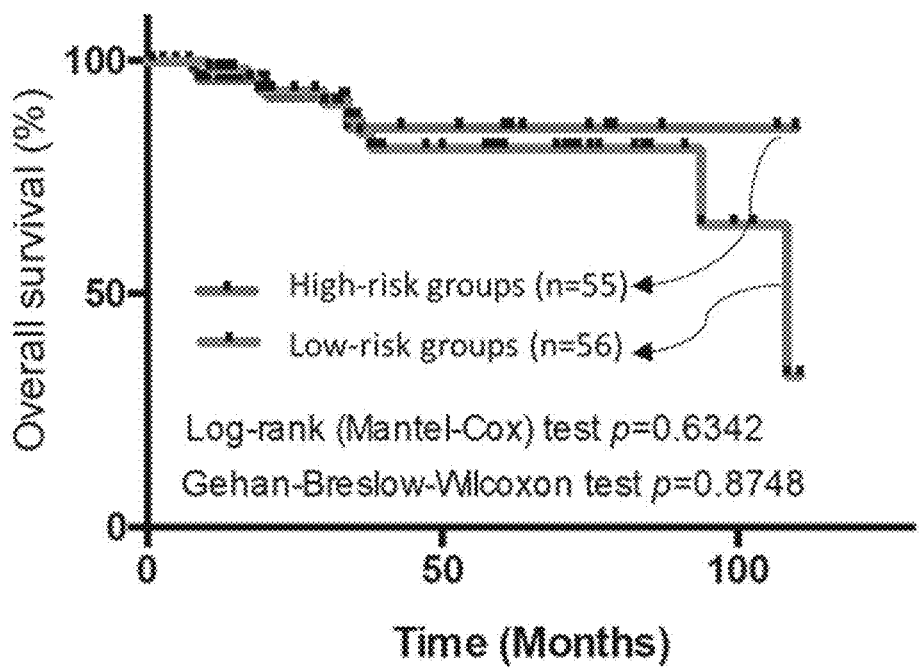
Figure 12D:
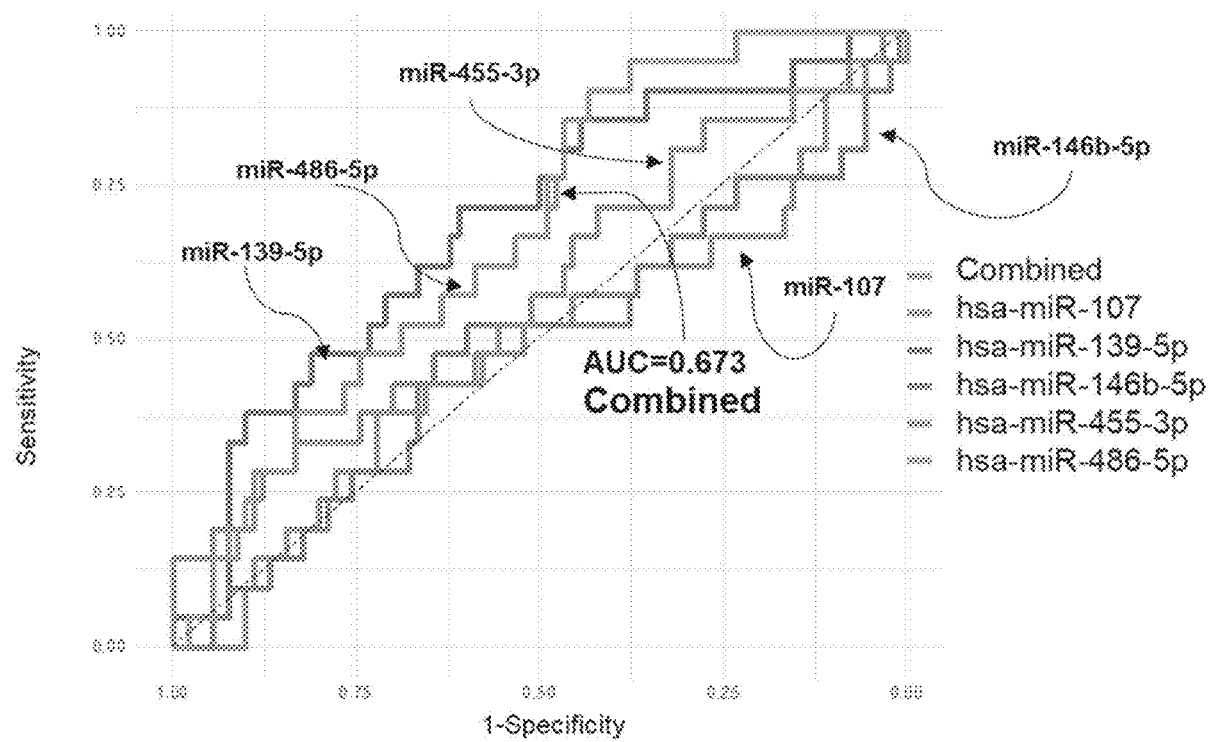

Previous studies did not investigate these 8 miRNAs as a signature to predict the relapse of TNBC patients. In addition, the 8-miRNA signature was analyzed for DFS and OS. The findings suggested that only hsa-miR-107, hsa-miR-146b-5p, hsa-miR-455-3p, hsa-miR-486-5p and hsa-miR-139-5p have statistical significance in TNBC patients. FIGS. 12A-12D show predictive value of the 5-miRNA signature for 111 TNBC patients. In FIG. 12A, the 5-miRNA signature risk score distribution in the DFS and OS of TNBC patients. "R" stands for recurrence; "NR" stands for nonrecurrence. The colorgram of 5-miRNA expression profiles of high- and low-risk groups with TNBC. The green line represents the median miRNA signature cutoff dividing patients into low- and high-risk groups. FIG. 12B shows Kaplan-Meier estimates of DFS in the training set. FIG. 12C shows Kaplan-Meier estimates of OS in the training set. FIG. 12D shows ROC for TNBC recurrence by the miRNA signature between patients with/without recurrence in the combined or respective miRNAs. The predictive value of the 5 combined miRNAs was no different than that of a single miRNA. The p-values were calculated using Log-rank and Gehan-Breslow-Wilcoxon tests. Accordingly, the 5-miRNA signature was used to predict the recurrence of patients, and a poor prognostic results, with an AUC of 0.673, was obtained.

Figure 13A:
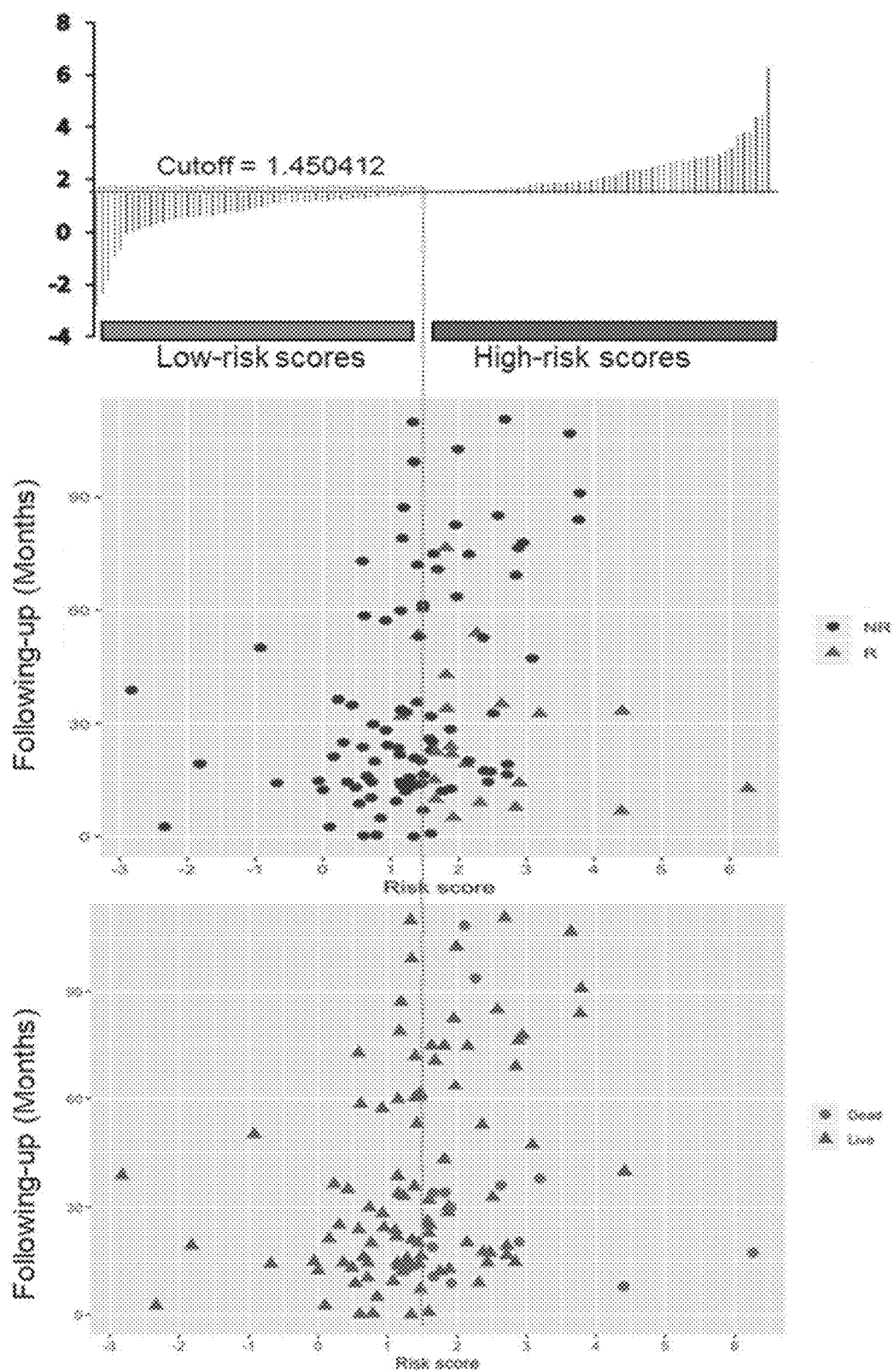
FIGS. 13A-13E show predictive value of the 7-miRNA signature for 111 TNBC patients.
Figure 13B:
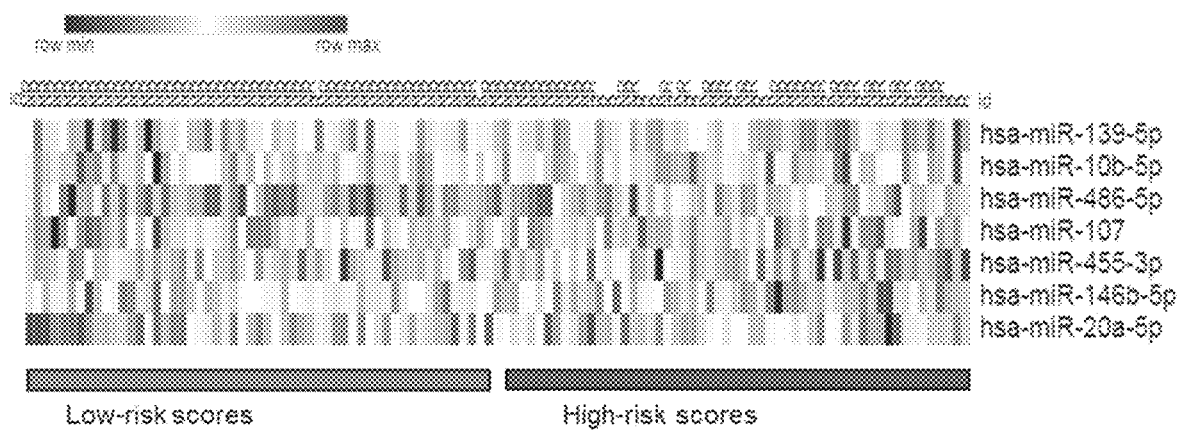
Figure 13C:
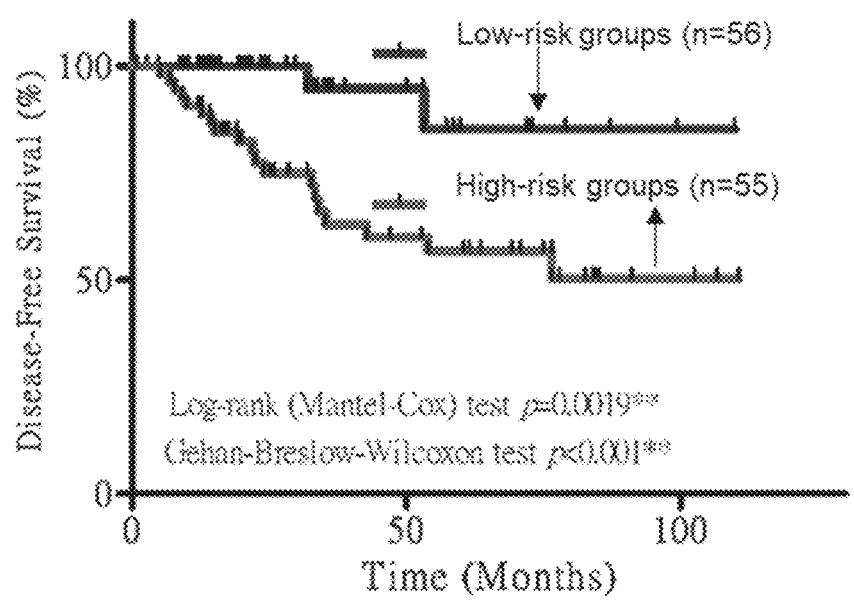
Figure 13D:
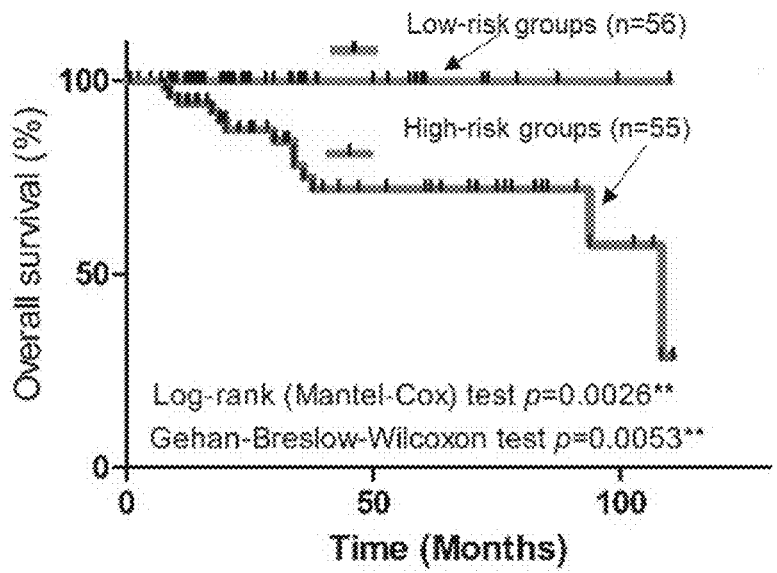
Figure 13E:
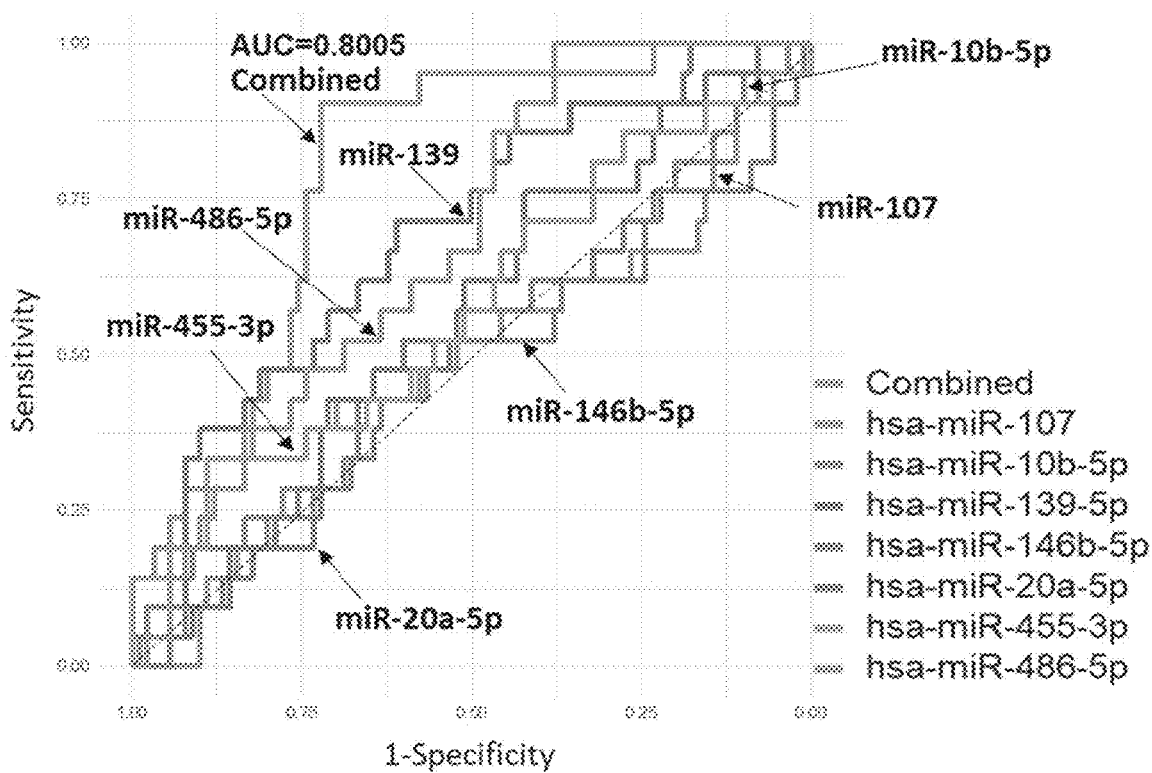

Similarly, a 7-miRNA signature was also tried to be calculated to predict the recurrence of TNBC patients. FIGS. 13A-13E show predictive value of the 7-miRNA signature for 111 TNBC patients. FIG. 13A shows the 7-miRNA signature risk score distribution in DFS and OS of TNBC patients. The colorgram of 7-miRNA expression profiles of high- and low-risk groups with TNBC is shown. The dash line represents the median miRNA signature cutoff dividing patients into the low- and high-risk groups. "R" stands for recurrence; "NR" stands for nonrecurrence. FIG. 13B shows the expression of heatmap in 8 miRNAs for 111 TNBC patients. FIG. 13C shows Kaplan-Meier estimates of DFS for the training set. FIG. 13D shows Kaplan-Meier estimates of OS for the training set. FIG. 13E shows ROC for TNBC recurrence by the miRNA signature between patients with/without recurrence in the combined or respective miRNAs. The 7 combined miRNAs had a stronger predictive value than a single miRNA. The p-values were calculated using Log-rank and Gehan-Breslow-Wilcoxon tests. Accordingly, the data showed that the 7-miRNA signature (AUC of 0.8032) has very similar accuracy to the 8-miRNA signature (AUC of 0.8005). Most of the genes are targeted by more than one miRNA, and these miRNAs may target the same or different genes in similar functional pathways.

These reasons lead to differences in the predictions according to the 5- or 8-miRNA signature based on RNA-RNA crosstalk and ceRNA-ceRNA regulation. Juan Xu et al. have provided constructive suggestions regarding miRNA-miRNA crosstalk. They consider miRNA crosstalk based on genomic similarity, regulatory networks, functions and phenomics. In addition, a growing number of studies have tried to investigate ceRNA-ceRNA regulation in specific cancer types. The ceRNA (competing endogenous RNAs) hypothesis assumes that the RNA transcript that covers miRNA response elements (MREs) can sequester miRNAs from other targets sharing the same MREs, thereby regulating their expression. Hence, the combined signature is crucial for cancer risk prediction since it integrates the multifactorial nature of cancer and tumorigenesis, which is imperative for the personalization of patient care.

Figure 14A:
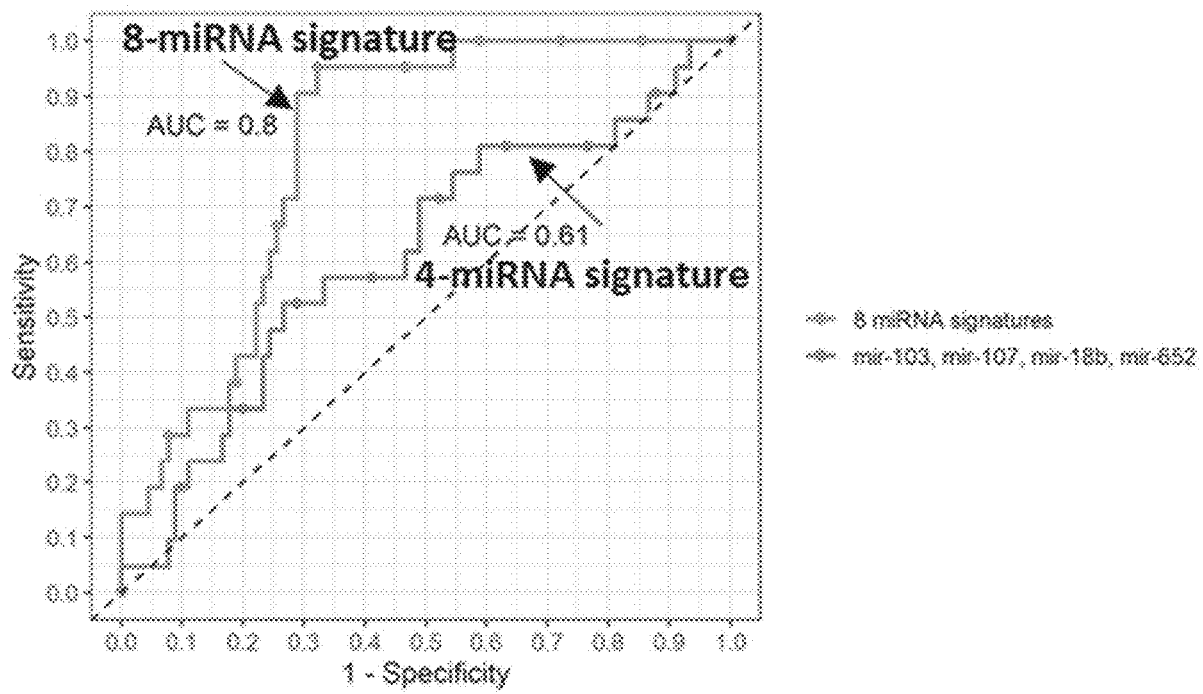
FIGS. 14A-14B show ROC for TNBC patient recurrence by the 4-miRNA signature.
Figure 14B:
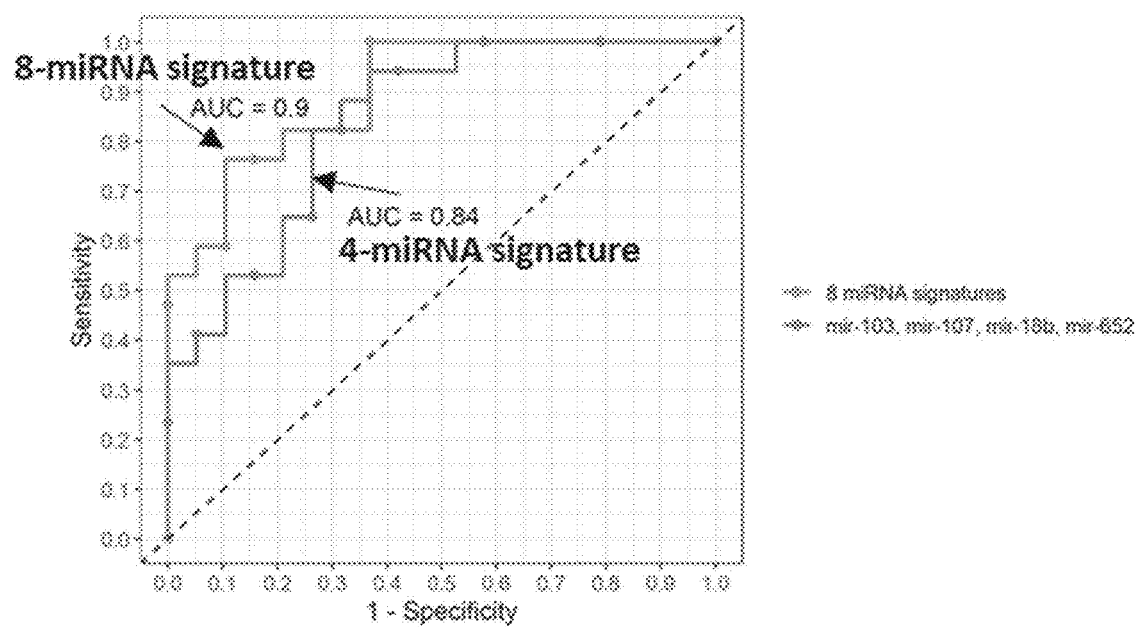

Libero Santarpia et al. demonstrated that a 4-miRNA signature (miR-18b, miR-103, miR-107, and miR-652) may assist in accurately predicting tumor relapse and OS in patients with TNBC. A ROC analysis by this 4-miRNA signature was performed and compared with the 8-miRNA signature described above. FIGS. 14A-14B show ROC for TNBC patient recurrence by the 4-miRNA signature. The ROC curves generated using the prognosis and expression levels of the 4-miRNA signature were able to discriminate between patients with relapse in 111 patients in TCGA_TNBC (FIG. 14A) and 36 patients in the E-MTAB-1989 and GSE19783 datasets (FIG. 14B). The AUC values were 0.61 and 0.84 by the 4-miRNA signature. Accordingly, FIGS. 14A-14B suggested that the 8-miRNA signature (hsa-miR-139-5p, hsa-miR-10b-5p, hsa-miR-486-5p, hsa-miR-455-3p, hsa-miR-107, hsa-miR-146b-5p, hsa-miR-324-5p, and hsa-miR-20a-5p) described above predicted DFS ability better than the 4-miRNA signature in TCGA_TNBC and combined GSE19783 and E-MTAB-1989 data.

Figure 15:
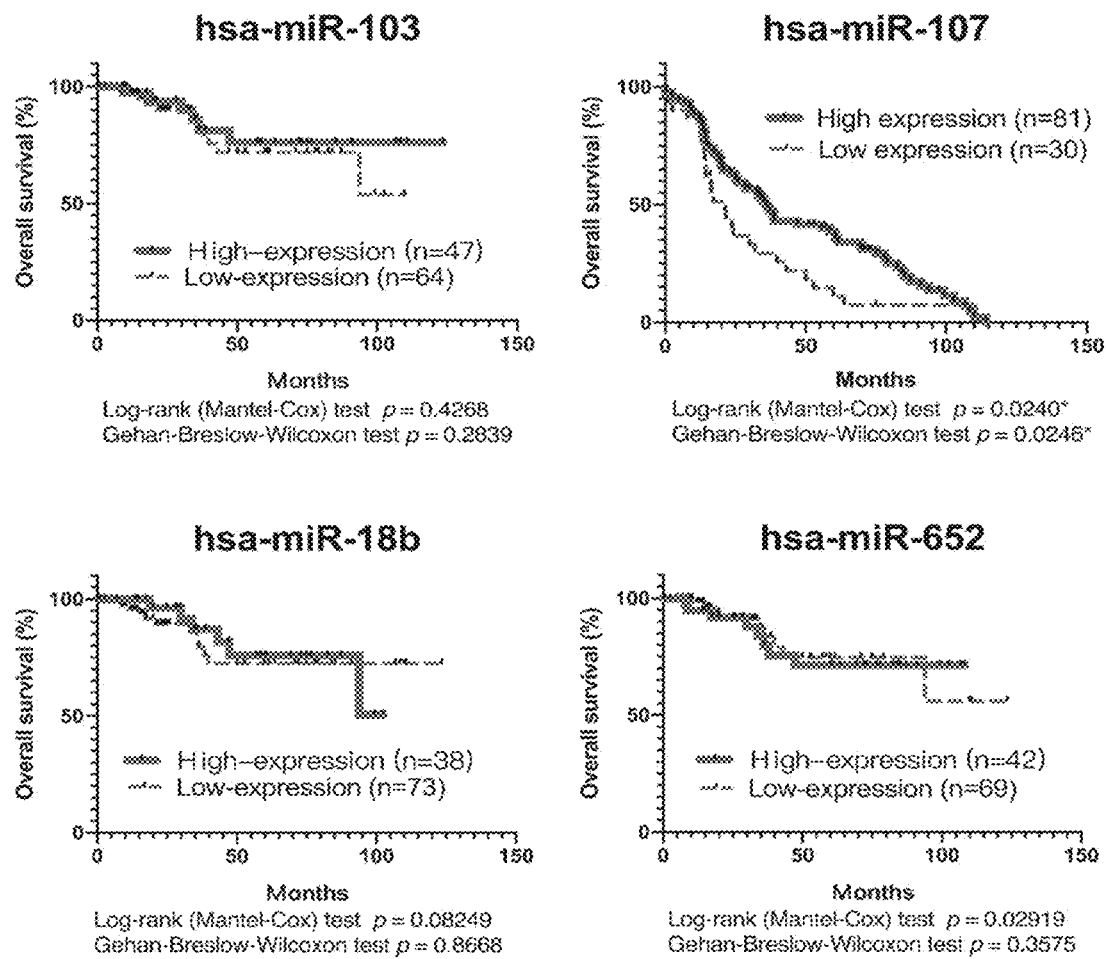
FIG. 15 shows Kaplan-Meier survival analysis estimates the OS of TNBC patients according to the 4-miRNA expression profile.

Additionally, Kaplan-Meier analysis of miR-18b, miR-103, miR-107, and miR-652 expression is shown in FIG. 15. FIG. 15 shows Kaplan-Meier survival analysis estimates the OS of TNBC patients according to the 4-miRNA expression profile. Relative levels of miR-18b, miR-103, miR-107, and miR-652 in 111 patients in TCGA_TNBC with their survival times. The p-values were calculated using Log-rank and Gehan-Breslow-Wilcoxon tests. *p<0.05. Accordingly, OS in TNBC patients with miR-107 expression levels of survival was significant.

Figure 16:
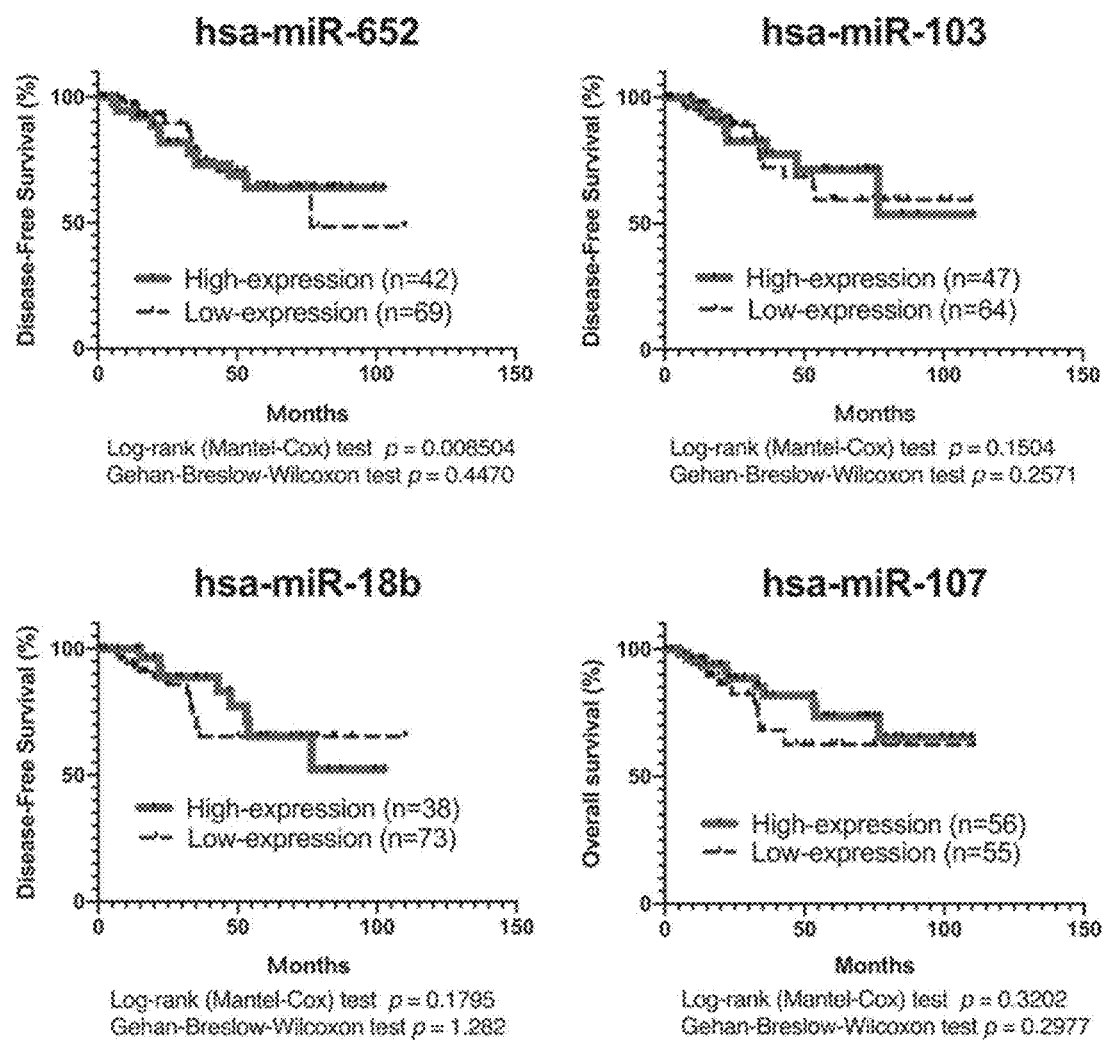
FIG. 16 shows Kaplan-Meier survival analysis estimates DFS of TNBC patients according to the 4-miRNA expression profile.

FIG. 16 shows Kaplan-Meier survival analysis estimates DFS of TNBC patients according to the 4-miRNA expression profile. Relative levels of miR-18b, miR-103, miR-107, and miR-652 in 111 patients in TCGA_TNBC with recurrence. The p-values were calculated using Log-rank and Gehan-Breslow-Wilcoxon tests. From FIG. 8, it can be found that no miRNAs in the DFS of TNBC patients were significant.

Figure 17A:
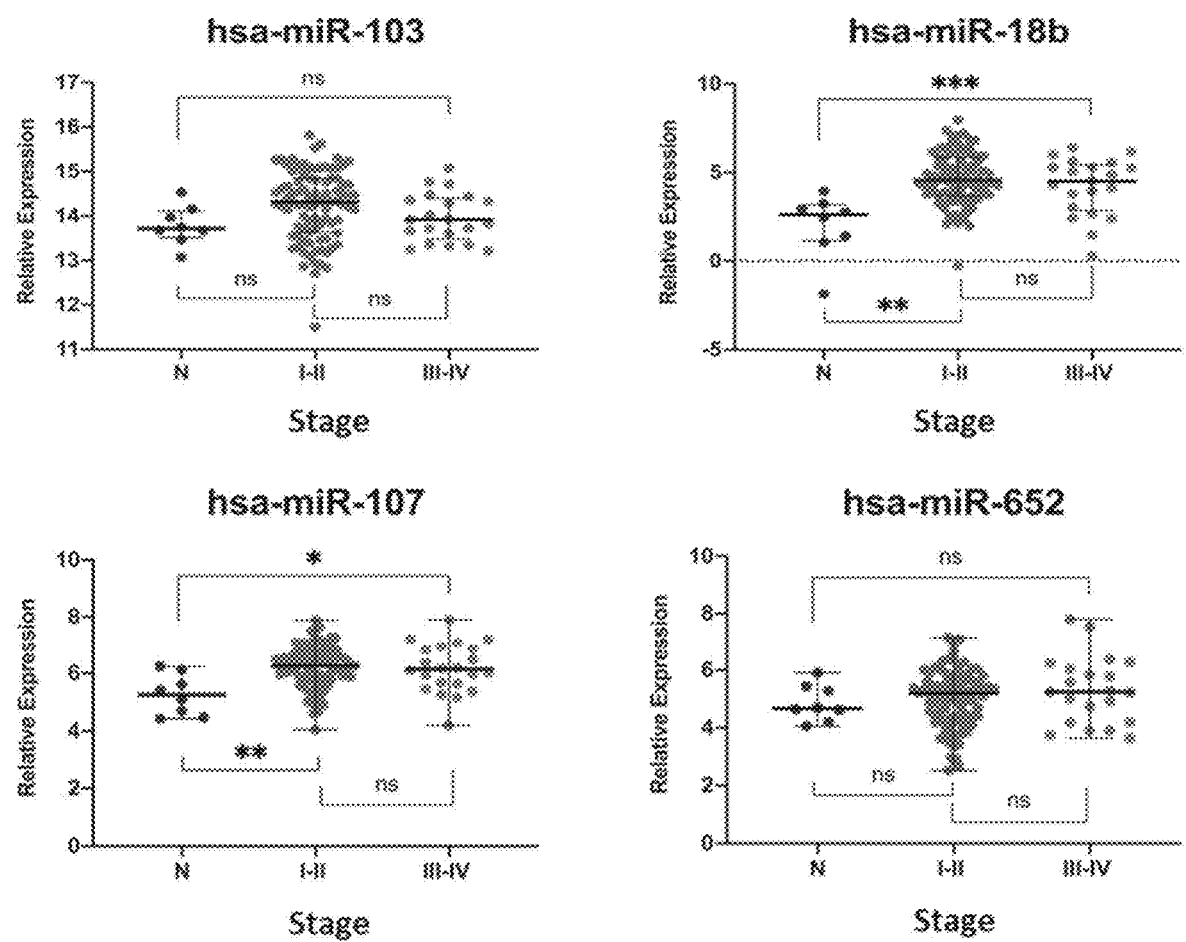
FIGS. 17A-17C show the difference in the 4-miRNA expression profiles in subgroups divided by TNM classification.
Figure 17B:
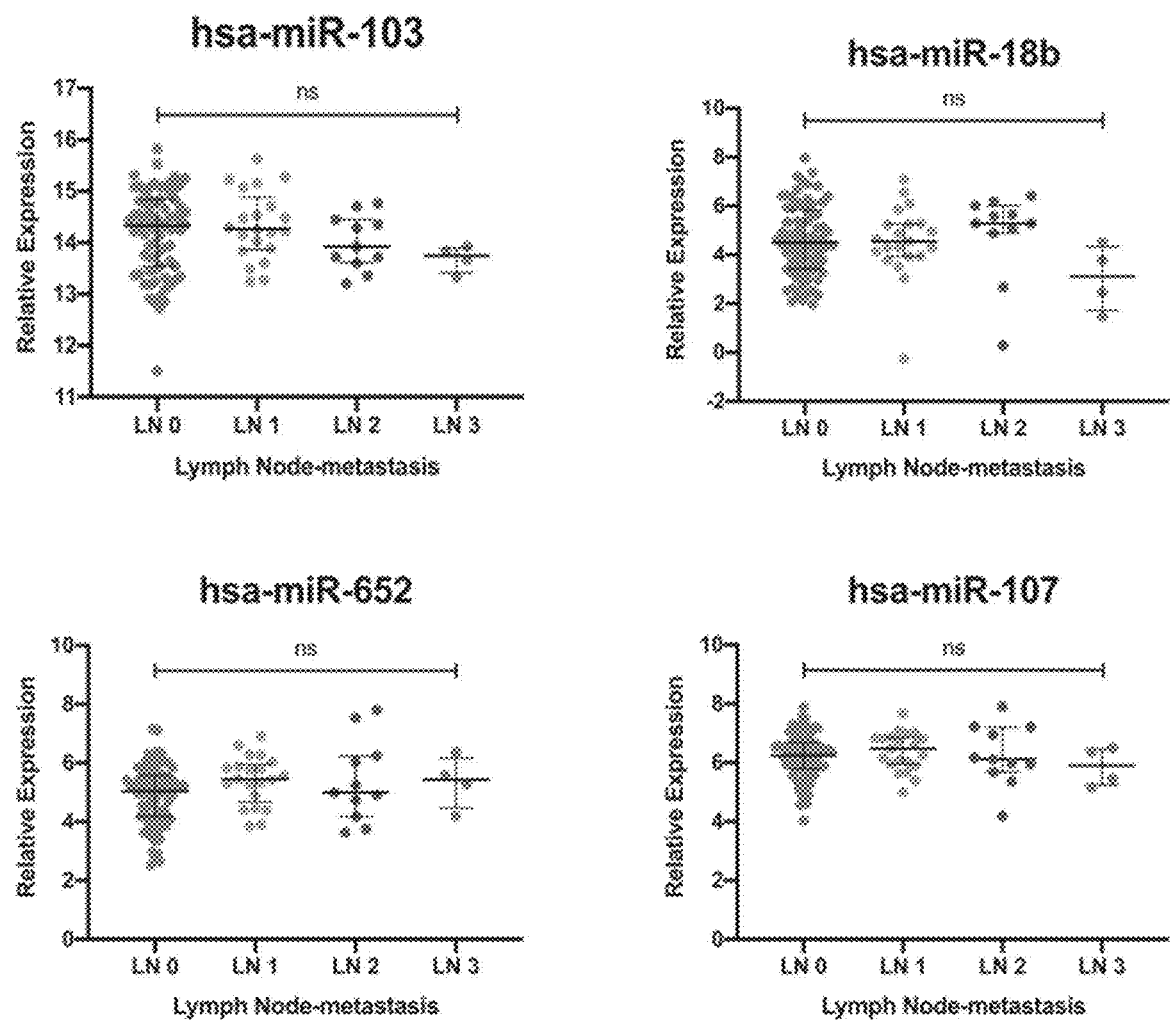
Figure 17C:
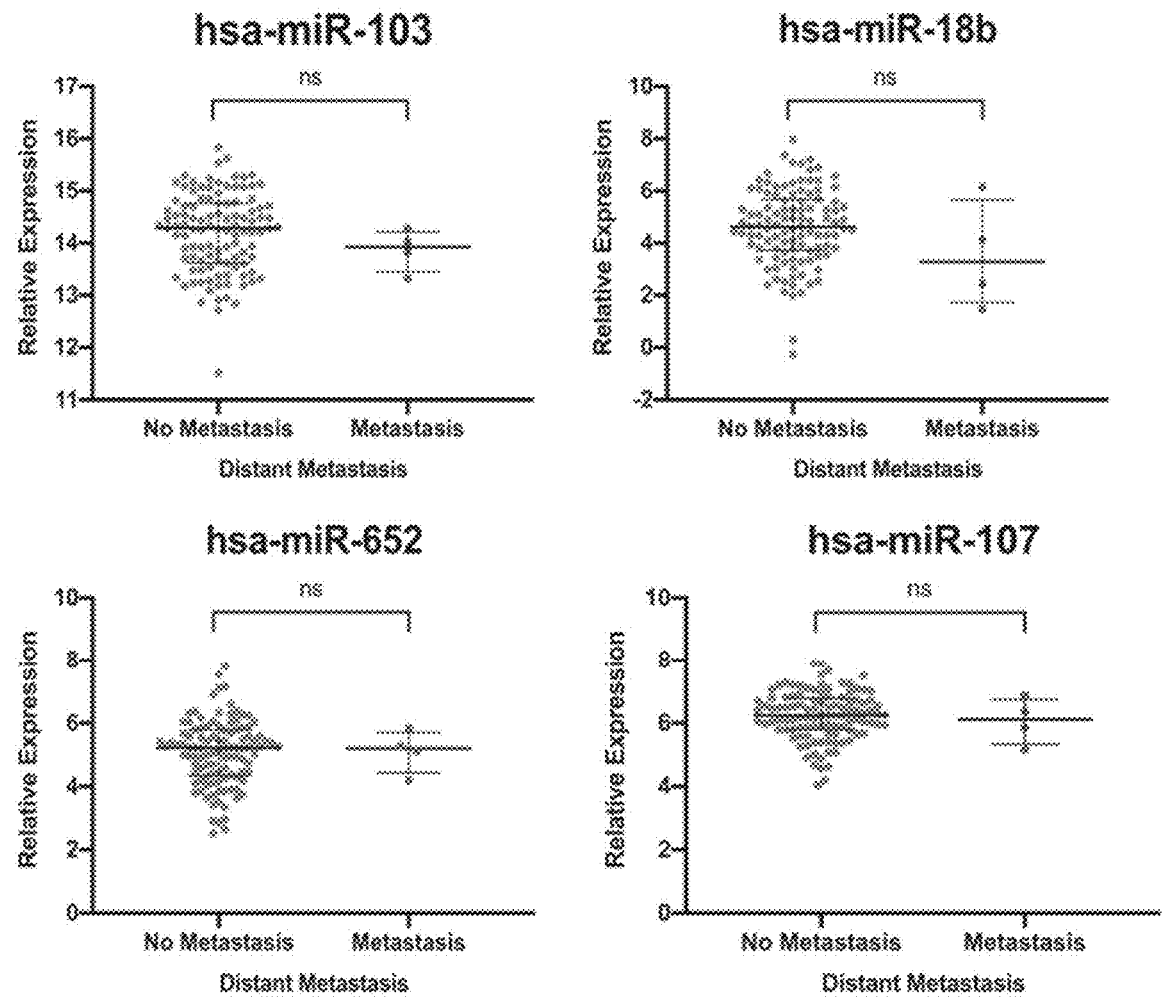

FIGS. 17A-17C show the difference in the 4-miRNA expression profiles in subgroups divided by TNM classification. FIG. 17A shows 111 TNBC patients with 8 N vs. 89 stage I-II vs. 22 stage III-IV. The p-values were calculated with TCGA_TNBC. FIG. 17B shows the 111 TNBC patients with 74 LN0 vs. 21 LN1 vs. 12 LN2 vs. 4 LN3. The p-values were calculated with the Kruskal-Wallis test. FIG. 17C shows 111 TNBC patients with 107 no metastasis vs. 4 metastasis. The p-values were calculated using Student's t-test. *$p<0.05$; $p<0.01$; *$p<0.0001$; ns is not significant. N: adjacent normal; T: tumor stage; LN: lymph node; M: metastasis.

The hsa-miR-139-5p was highly correlated with tumor-node-metastasis (TNM) stage and was able to distinguish between different stages (I-II vs. III-IV stage, $p<0.05$), nodes (LN0, LN1, LN2 and LN3, $p<0.05$), and metastasis (no metastasis vs. metastasis, $p<0.05$). Several lines of evidence suggested that miR-139-5p is a prognostic biomarker for different cancer types. For example, the EZH2/miR-139-5p axis impeded EMT and lymph node metastasis (LNM) in pancreatic cancer. The hsa-miR-139-5p was downregulated VEGFR to inhibit signaling pathways in the development of esophageal cancer. The hsa-miR-139-5p could as anti-oncomiR to suppress primary malignant brain tumor progression by targeting the insulin-like growth factor 1 receptor (IGF-1R), associate of Myc 1 (AMY-1) and peroxisome proliferator-activated receptor y coactivator 1β (PGC-1β), thus inhibiting the PI3K/AKT and c-Myc signaling pathways. The tumor suppressor function of the miR-139-5p involved targeting HOXA10 to inhibit endometrial cancer cell growth and migration. MiR-139-5p was able to regulate the cell motility and invasion of aggressive breast cancer through the TGF-β, Wnt, Rho, and MAPK/PI3K signaling cascades. The hsa-miR-139-5p directly binds Rho-associated coiled-coil-containing protein kinase 2 (ROCK2) to suppress cell proliferation and invasion in ovarian cancer (OC). Many studies have identified that the miR-139-5p expression level could serve as a diagnostic, prognostic and therapeutic marker in the future. In addition, low expression was correlated with poor prognosis in hepatocellular carcinoma (HCC) and glioblastoma multiforme (GBM). However, further research with larger samples and studies is still needed to elucidate the functions of the miR-139-5p.

MiRNAs not only play a pivotal role in tumor differentiation but also contribute to biological processes in TNBC. Functional enrichment of the 8-miRNA signature was analyzed with Hallmark and Gene Ontology (GO) annotations. The combined results showed that these miRNAs were highly correlated with inflammatory regulation, tumor metastasis, and metabolism. Many reports confirm that TNBC exhibits the strongest immunogenicity and may provide an option for immunotherapy. For example, CD4+ helper T-cells have an immune response pathway via Th1 and Th2 in ER-negative breast cancer. Type I immunity, such as CD4+ T cells, secrete cytokines (TNF-α, IFN-Y, CD8+, and IL-2 cytotoxic T cells) to support the destruction of the tissue environment. Moreover, tumor-associated macrophages (TAMs) are composed of M1 and M2 phenotypes and are correlated with macrophage polarization, cytokine profiles and migratory functions. Hartman et al. demonstrated that an effective treatment strategy involved suppressing both IL-6 and IL-8 in TNBC. Hence, recent evidence has suggested that activated immune response genes are associated with good prognosis. Furthermore, a recent clinical trial used pembrolizumab, which is a high-affinity anti-PD-L1 antibody, in metastatic TNBC patients who present PD-L1 expression. PD-L1 can bind and activate cytotoxic T-cells to prevent T-cell activation and proliferation as well as the release of IL-2. PD-L1 is an important regulatory checkpoint since it prevents excessive adaptive immune responses. Metastasis in breast cancer is characterized by a distinctive spread via regional lymph nodes to the lungs, liver, brain, and bones. Increasing evidence shows that miRNAs are involved in a variety of processes contributing to tumorigenesis and metastasis in TNBC. In recent studies of metastatic breast cancer, hsa-miR-10b, hsa-miR-20a, hsa-miR-139-5p, and hsa-miR-486-5p were highly expressed in lymph node metastases. In addition, MUC1, which is a cell wall-based mucin glycoprotein present on the apical surface of epithelial cells, is highly expressed in many adenocarcinomas. Pillai K et al. demonstrated that overexpression of MUC1 is associated with angiogenesis and chemoresistance in cancer.

Overall, the evidence indicates that this 8-miRNA signature can accurately predict the relapse of TNBC patients and that it is important for further clinical prognosis. Hence, it is possible to accurately identify clinical outcomes in TNBC patients using an 8-miRNA signature. The 8-miRNA signature could be useful in TNBC according to risk in trials involving the adjuvant treatment of patients. Further validation studies in large independent patient cohorts are needed to assess the true clinical value of our findings for TNBC diagnosis and prognosis.

Abbreviations

BC: breast cancer; TNBC: triple-negative breast cancer; Non-TNBC: non-triple-negative breast cancer; ER: estrogen receptor; PR: progesterone receptor; HER2: human epidermal growth factor receptor 2; MDR: multi-drug resistance; DFS: disease-free survival; OS: overall survival; miRNA: microRNA; EMT: epithelial-to-mesenchymal transition; CSC: stem cell-like properties; NGS: next-generation sequencing; TNM: tumor-node-metastasis; TCGA: The Cancer Genome Atlas; GEO: Gene Expression Omnibus; RPM: reads per million; GMM: Gaussian mixture model; GSEA: gene set enrichment analysis; ROC: receiver operating characteristic; AUC: area under the curve; GO: Gene Ontology; WHO: World Health Organization; LN: lymph node; CeRNA: competitive endogenous RNAs.

The reader's attention is directed to all papers and documents which are filed concurrently with this specification and which are open to public inspection with this specification, and the contents of all such papers and documents are incorporated herein by reference.

What is claimed is:

1. A method of predicting a risk of cancer recurrence in a triple-negative breast cancer (TNBC) patient by a signature of miRNA gene products, the method comprising:

providing a breast cancer sample from the TNBC patient, the breast cancer sample negatively expressing biomarkers comprising estrogen (ER), progesterone (PR), and human epithelial receptor 2 (HER2) determined by immunohistochemical staining;

measuring an expression level of each of a combination of miRNAs in the breast cancer sample, wherein the combination of miRNAs consists of hsa-miR-139-5p, hsa-miR-10b-5p, hsa-miR-486-5p, hsa-miR-455-3p, hsa-miR-107, hsa-miR-146b-5p, hsa-miR-324-5p, and hsa-miR-20a-5p;

calculating a risk score based on the expression level of the miRNAs, wherein the risk score=(0.02554×an expression value of miR-139)+(−0.000005284×an expression value of miR-10b)+(−0.0003305×an expression value of miR-486)+(0.008664×an expression value of miR-107)+(0.003201×an expression value of miR-324)+(0.001031×an expression value of miR-455)+(0.000474×an expression value of miR-146b)+(−0.001575×an expression value of miR-20a); and comparing the risk score with a reference threshold of 1.602 to determine the risk of cancer recurrence of the TNBC patient, wherein the TNBC patient is predicted to have a high risk when the risk score is equal to or larger than 1.602.

* * * * *

SEQUENCE LISTING

```
<160> NUMBER OF SEQ ID NOS: 8

<210> SEQ ID NO 1
<211> LENGTH: 23
<212> TYPE: RNA
<213> ORGANISM: Homo sapiens
<220> FEATURE:
<221> NAME/KEY: misc_RNA
```

<222> LOCATION: (1)..(8)

<400> SEQUENCE: 1
uacccuguag aaccgaauuu gug          23

<210> SEQ ID NO 2
<211> LENGTH: 23
<212> TYPE: RNA
<213> ORGANISM: Homo sapiens

<400> SEQUENCE: 2
ucuacagugc acgugucucc agu          23

<210> SEQ ID NO 3
<211> LENGTH: 22
<212> TYPE: RNA
<213> ORGANISM: Homo sapiens

<400> SEQUENCE: 3
uccuguacug agcugccccg ag           22

<210> SEQ ID NO 4
<211> LENGTH: 21
<212> TYPE: RNA
<213> ORGANISM: Homo sapiens

<400> SEQUENCE: 4
gcaguccaug ggcauauaca c            21

<210> SEQ ID NO 5
<211> LENGTH: 23
<212> TYPE: RNA
<213> ORGANISM: Homo sapiens

<400> SEQUENCE: 5
uaaagugcuu auagugcagg uag          23

<210> SEQ ID NO 6
<211> LENGTH: 23
<212> TYPE: RNA
<213> ORGANISM: Homo sapiens

<400> SEQUENCE: 6
agcagcauug uacagggcua uca          23

<210> SEQ ID NO 7
<211> LENGTH: 22
<212> TYPE: RNA
<213> ORGANISM: Homo sapiens

<400> SEQUENCE: 7 cgcaucpccu agggcauugg ug           22

<210> SEQ ID NO 8
<211> LENGTH: 23
<212> TYPE: RNA
<213> ORGANISM: Homo sapiens

<400> SEQUENCE: 8
ugagaacuga auuccauagg cug          23